(12) United States Patent
Lai

(10) Patent No.: US 11,464,406 B2
(45) Date of Patent: Oct. 11, 2022

(54) SUBJECTIVE WAVEFRONT REFRACTION USING CONTINUOUSLY ADJUSTABLE WAVE PLATES OF ZERNIKE FUNCTION

(71) Applicant: Shui T. Lai, Windermere, FL (US)

(72) Inventor: Shui T. Lai, Windermere, FL (US)

(\*) Notice: Subject to any disclaimer, the term of this patent is extended or adjusted under 35 U.S.C. 154(b) by 333 days.

(21) Appl. No.: 16/544,886

(22) Filed: Aug. 19, 2019

(65) Prior Publication Data

US 2020/0077885 A1  Mar. 12, 2020

Related U.S. Application Data

(60) Continuation of application No. 15/137,243, filed on Apr. 25, 2016, now Pat. No. 10,383,512, which is a division of application No. 12/790,977, filed on May 31, 2010, now Pat. No. 9,320,426, which is a division of application No. 11/746,051, filed on May 8, 2007, now Pat. No. 7,726,811, and a continuation-in-part of application No. 11/675,079, filed on Feb. 14, 2007, now Pat. No. 7,699,471.

(60) Provisional application No. 60/746,772, filed on May 8, 2006, provisional application No. 60/773,758, filed on Feb. 14, 2006.

(51) Int. Cl.
*A61B 3/036* (2006.01)
*A61B 3/00* (2006.01)
*G02C 7/02* (2006.01)
*A61B 3/032* (2006.01)

(52) U.S. Cl.
CPC .......... *A61B 3/036* (2013.01); *A61B 3/0008* (2013.01); *A61B 3/0025* (2013.01); *A61B 3/032* (2013.01); *G02C 7/02* (2013.01)

(58) Field of Classification Search
CPC ....... A61B 3/036; A61B 3/032; A61B 3/0025; A61B 3/0285; A61B 3/0008; A61B 3/18; A61B 3/1015; A61B 3/028; A61B 3/0033; A61B 3/0083; A61B 3/04; A61B 3/1035; A61B 3/14; A61B 3/0058; A61B 3/152; A61B 3/0041; A61B 3/02; A61B 3/0325; A61B 3/145; G02C 7/02; G02C 7/027; G02C 2202/22; G02C 13/003; G02C 7/085; G02C 7/10; G02B 26/005; G02B 3/14
See application file for complete search history.

(56) References Cited

U.S. PATENT DOCUMENTS

2007/0258046 A1\* 11/2007 Lai ....................... A61B 3/0008
351/159.73

\* cited by examiner

*Primary Examiner* — Brandi N Thomas
(74) *Attorney, Agent, or Firm* — SF Bay Area Patents, LLC; Andrew V. Smith

(57) ABSTRACT

A wavefront device produces adjustable amplitudes in optical path differences and adjustable axis orientation angles. two substantially identical wave plates have a wavefront profile of at least the third order Zernike polynomial function which are not circularly symmetric, as denoted by Z(i,j) where i≥3 and j≠0. The wave plates are mounted in rotatable mounts with their optical centers substantially aligned with each other. An subjective wavefront refraction instrument and method are provided to correct low and high order aberrations of the eye, using the adjustable wave plates that have astigmatism and higher order Zernike function optical path difference wavefront profiles.

20 Claims, 11 Drawing Sheets

SUBJECTIVE WAVEFRONT REFRACTION USING CONTINUOUSLY ADJUSTABLE WAVE PLATES OF ZERNIKE FUNCTION

PRIORITY

This application is a Continuation of U.S. patent application Ser. No. 15/137,243, filed Apr. 25, 2016, now U.S. Pat. No. 10,383,512; which is a Divisional of U.S. patent application Ser. No. 12/790,977, filed May 31, 2010, now U.S. Pat. No. 9,320,426; which is a Divisional of U.S. patent application Ser. No. 11/746,051, filed May 8, 2007, now U.S. Pat. No. 7,726,811; which claims the benefit of priority to U.S. provisional patent application No. 60/746,772, filed May 8, 2006, and is a Continuation in Part (CIP) of U.S. patent application Ser. No. 11/675,079, filed Feb. 14, 2007, now U.S. Pat. No. 7,699,471; which claims priority to U.S. provisional patent application No. 60/773,758, filed Feb. 14, 2006.

BACKGROUND

Before the advent of the wavefront aberrometer, many patients' visual symptoms were collectively referred to as a result of "irregular astigmatism". Increasingly, more ophthalmologists and optometrists have begun measuring wavefront errors of patients' eye. A wealth of information is now available, that was not heretofore, from autorefractor or cornea topography measurements. Use of a wavefront map as a diagnosis tool is also gaining popularity, and vision care professionals use it to explain diagnoses to patients having visual complaints.

It is useful to understand the source of a problem. However, patients are most interested in solutions; such as getting rid of visual complaints, and improving their quality of vision. Currently, laser refractive surgery, such as LASIK, is one possible solution. However, laser surgery is invasive and the tissue healing process following surgery can induce its own set of aberrations, often rendering an attempt to correct the pre-operation errors fruitless. It has been proposed to correct high order aberrations (HOA) with non-invasive devices such as spectacles or contact lenses.

It was proposed in US application 2004/0160576A1, which is hereby incorporated by reference, to identify high order wavefront errors with a patient feedback control process. However, lacking in that disclosure is the basis for a patient to adjust each of the wavefront components. The '160576 application does disclose use of visual acuity as a measure to find an end point. As it was pointed out in the '160576 application, an acuity chart, or Snellen letter chart, is not an ideal target for wavefront optimization. More importantly, no method is presented regarding how a patient may choose which Zernike function to vary among the dozens of Zernike functions, without which the patient would have to go on a random walk, using by trial and error on all or substantially all of the Zernike functions. Without a clear step by step procedure, a patient may not even be able to find an optimal sphere, cylinder and axis, much less the high order Zernike components, wherein the effect of those aberrations on acuity is much smaller. The patient might get totally lost in the process, and it might take hours to come to any final optimized combination, if it ever got there at all.

RECOGNIZED BY THE INVENTOR

Improving quality of vision is more complicated than measuring the HOA and canceling them. Higher order aberrations are typically much smaller in amplitude compared to the defocus and astigmatism terms, and they vary from eye to eye. The question arises as to whether there would be visual benefits by correcting them in some patients. Also, the brain plays a key part in interpreting and in forming perceived images of what one sees. The optical image formed at the retina is only a starting point.

If one can measure the HOA; then one can cancel them optically. However, as it was pointed out, it is not clear whether if this cancellation results in improvement in one patient, then the same approach will work for a different patient.

In embodiments described herein, tools are provided for performing a subjective method for a patient. In a preferred embodiment, not just the sphere and cylinder and axis are handled, but the HOA errors are refracted as well. That is, using a technique in accordance with a preferred embodiment, a patient can actually see through a combination of wave plates that are adjustable in amplitude, and preferably also in angle. With this technique, a patient can actually see whether a wavefront correction, as presented to the patient, provides any benefits. A subjective technique in accordance with a preferred embodiment stands in contrast with objective techniques in which HOA errors of an eye are measured and a spectacle or contact lens is provided to cancel the HOA, and wherein the patient finds out only later if the device offers any benefits at all when he or she receives the corrective device.

In a preferred embodiment, an instrument is provided that comprises wave plates of Zernike functions, each of which is continuously adjustable in amplitude, and preferably also in angle. In addition, a continuously variable wave plate assembly is alternatively provided for utilizing a series of wave plates in small increment steps. These wave plates can be arranged on a disk, like a series of lenses in a phoropter, and the system can be made affordable for most eye care professionals.

SUMMARY OF THE INVENTION

A wavefront device that produces adjustable amplitudes in optical path differences and adjustable axis orientation angles is provided. Two substantially identical wave plates have a wavefront profile of at least the third order Zernike polynomial functions which are not circularly symmetric, as denoted by $Z(i,j)$ where $i \geq 3$ and $j \neq 0$. The wave plates are mounted in rotatable mounts with their optical centers substantially aligned with each other.

The device may include a pinion gear engaging with bevel gears including at least one bevel gear attached to each of the rotatable mounts, wherein rotating the pinion gear may cause the wave plates to rotate in opposite direction at a substantially equal angular rate to cause a change in amplitude of the device. Electric motors with drive mechanisms may drive the wave plates at a same angular rate substantially in synchronization, while the wave plates move in equal amount and in opposite direction to change a wavefront amplitude. The wave plates are moved in a same direction to change an optic axis angle direction.

A method of generating a subjective optical prescription with a Zernike wave plate having an ability to substantially continuously adjust its amplitude and optic axis angle is also provided. Two substantially identical wave plates have a wavefront profile of a Zernike polynomial function. Optical centers of the wave plates are aligned. The wave plates are rotated in opposite direction in one or more substantially identical angular amounts until a patient indicates an optimal setting. The entire assembly is rotated including the two wave plates to an optic axis angle indicated as optimal by the patient. An optical prescription is generated based on initial positions and rotation amounts of the two wave plates. The rotating of the two wave plates may include rotating a pinion gear which engages with bevel gears that are mounted with the wave plates.

A method of determining second order and higher order aberrations of a patient's eye is also provided. Zernike functions are provided in a predetermined order in a priority list. At least one point source is provided as a viewing target. A first adjustable wave plate is selected according to the order in the priority list. The first adjustable wave plate is placed in a patient's line of sight. A refractive error of the patient is minimized by adjusting amplitude and angle of the first adjustable wave plate while the patient is looking at the viewing target. These are repeated for one or more further wave plates according to the order in the priority list, until no appreciable further improvement in image quality of the point source is observed by the patient.

The priority list may include $Z(2,0)$, $Z(2,+/-2)$, and $Z(3,+/-1)$, in that order, and may further include $Z(3+/-3)$ after $Z(3, +/-1)$, and may further include $Z(4,+/-2)$, $Z(5,+/-1)$, $Z(4,+/-4)$, $Z(5,+/-3)$, $Z(6,+/-2)$, $Z(6,+/-4)$, $Z(5,+/-5)$, in that order, after $Z(3+/-3)$. The placing of the first adjustable wave plate may include positioning the first wave plate of the Zernike function at a conjugate corneal or pupil plane of the patient.

Refractive errors of third or higher order Zernike function aberrations may also be minimized. An input device is provided to the patient. An optic axis angle of an adjustable wave plate of third or higher order Zernike profile which is disposed at a conjugate corneal or pupil plane of the patient is varied while the patient is looking at the viewing target. An amplitude of the adjustable wave plate of third or higher order is varied also while the patient is looking at the viewing target. An indication is received from a patient that a predetermined end point has been reached by activation of the input device, The method may also include varying the angle of the wave plate of third or higher order, finding an optimal angle position, and then varying the amplitude of the adjustable wave plate. The predetermined end point may include a sharpest image of the point source target as indicated by the patient.

Contact or intraocular lenses may be provided and/or an ablation profile of refractive surgery may be determined such as for LASIK, PRK, LASEK, and/or intra-corneal surgery.

A method of correcting refractive errors of second and higher order aberrations of an eye is also provided. Second order aberrations are determined using adjustable $Z(2,0)$ and $Z(2,+/2)$ Zernike wave plates. Higher orders aberrations are corrected using $Z(2,0)$ and higher Zernike terms, wherein $Z(2,0)$ substantially corrects aberrations of all higher order Zernike terms that are spherically symmetric.

A further device for determining or correcting aberrations of an eye is also provided. The device includes at least one adjustable wave plate having adjustable amplitude and optic axis angle. A priority list of Zernike functions is provided such that adjustable wave plates may be selected in accordance with an order of Zernike functions in the list. A point source is provided as a viewing target. The one or more selected wave plates are placed at a conjugate corneal or spectacle plane of a patient's eye. A patient searches for predetermined image end points while looking at the point source while angle and amplitude of the selected wave plate are varied.

The priority list may include $Z(2,0)$, $Z(2,+/-2)$, and $Z(3,+/-1)$, in that order, and may further include $Z(3+/-3)$ after $Z(3, +/-1)$, and may further include $Z(4,+/-2)$, $Z(5,+/-1)$, $Z(4,+/-4)$, $Z(5,+/-3)$, $Z(6,+/-2)$, $Z(6,+/-4)$, $Z(5,+/-5)$, in that order, after $Z(3+/-3)$. The placing of the first adjustable wave plate may include positioning the first wave plate of the Zernike function at a conjugate corneal or pupil plane of the patient.

The ordering of the priority list may be modified according to an aberration amplitude of the patient's eye in Zernike function as determined by a subjective wavefront aberrometer. The priority list may be modified by a condition of the patient's eye, including a keratoconus and/or a corneal transplant condition. The priority list may be modified by weighting factors with relative values affecting the ordering of the list as determined by the clinical experience of a physician.

The adjustable wave plate may include adjustable wave plates $Z(2,0)$ and $Z(2,+/-2)$, and/or another wavefront device such as liquid crystal wave plates or deformable mirrors. The other wavefront device may produce adjustable amplitudes in optical path differences and adjustable axis orientation angles, and include two substantially identical wave plates with wavefront profile of at least the third order Zernike polynomial function, which are not circularly symmetric, as denoted by $Z(i,j)$ where $i \geq 3$ and $j \neq 0$. The wave plates may be mounted in rotatable mounts with their optical centers substantially aligned with each other.

The adjustable wave plate may include at least one substantially identical pair of wave plates having a Zernike function optical path difference profile, a deformable mirror and/or a liquid crystal wave plate.

An optical instrument is also provided for generating a prescription for one or more corrective lenses or corrective procedures for a patient by subjective refraction. The instrument includes a stable frame having a defocus corrector assembly (DCA) and an astigmatism corrector assembly coupled thereto. The DCA causing a change of defocus power at the patient's eye, and includes a first motor and at least two DCA lenses disposed along an optical axis between an image source and the patient's eye. At least one of the DCA lenses is movable relative to the frame along the optical axis for adjusting defocus power and/or is replaceable with one or more further lenses with incremental dioptric powers. The defocus power may be thereby measurably adjustable until the patient indicates that an initially blurry view of the image source has become substantially sharp. The ACA causes a change of astigmatism power, and includes a second motor and at least two astigmatism plates disposed along the optical axis that are relatively rotationally adjustable and/or wherein at least one of the ACA astigmatism plates is replaceable with one or more further cylindrical lenses. The astigmatism power is thereby measurably adjustable until the patient indicates that an initially elongate view of the image source has become substantially round.

The instrument may further include electrical and/or electronics hardware and/or computer programs for performing individually or collectively one or more of the following tasks:

(i) drive movement of one or more optical elements in the DCA or ACA, or both, to change defocus or astigmatism power, or both;

(ii) display a location of an optical element;

(iii) convert a location or orientation reading, or both, to a refractive power in units of diopters;

(iv) collect data relating to adjustments to the DCA and ACA;

(v) set limits of movement range for the DCA or ACA or both to avoid over-correction;

(vi) automatically advance DCA or ACA refractive power, or both, when such task is requested; or (vii) automatic align the ACA optical axis when such task is requested, or combinations thereof.

The ACA may provide a variable astigmatism correction amplitude or variable axis angle, or both. The ACA may include a first wave plate having a second order Zernike polynomial of astigmatism wavefront correction profile in an x-y plane. A second wave plate may have a second order Zernike polynomial of astigmatism wavefront correction profile in the x-y plane. The first and the second wave plates may be mounted with their wavefront profile origins aligned along an axis (Z-axis). One or more of the wave plates may be angularly adjustable with respect to said Z-axis. The wavefront profile of the Zernike polynomial of astigmatism of the first and second wave plates may include $Z(2,2)$ or $Z(2,-2)$. Both of the wave plates may be angularly adjustable with respect to the Z-axis.

First and second ACA astigmatism plates may be mounted on first and second rotary ball bearings, and first and second bevel gears may be coupled to the first and second ball bearings. A first pinion gear may drive the first and second bevel gears for oppositely rotating the first and second ACA plates. A second motor may drive the first pinion gear. A rotary angle sensing device may be coupled to a rotary encoder. A second pinion gear may be mounted between the first and second bevel gears.

The ACA may be further for causing a change in orientation of axis angle. At least two astigmatism plates of said ACA may be rotatable together as a whole. The optical instrument may further include third and fourth ball bearings coupled to the first and second ball bearings, respectively, and to the frame. A third bevel gear may be coupled to at least one of the third and fourth ball bearings. A third motor may be for rotating the astigmatism plates of the ACA assembly together. A second rotary encoder may be coupled to a fourth pinion gear for sensing angular rotation of the ACA assembly.

The instrument may include an optics holder for each of the DCA lenses. A linear slide may be coupled to the optics holder of at least one of the DCA lenses. A motor and lead screw may move the linear slide.

A computer program product may include a processor and a computer program for calculating amplitudes of the ACA plates from relative and/or absolute angular movement and/or for calculating diopter power of the DCA. Readable results may be output. The computer program product may also form an ordered list of decreasing significance of Zernike functions based on RMS amplitude of a patient's measured wavefront errors. The computer program product may also control measurements according to the ordered list. Measurements for Zernike functions having a RMS amplitude less than 0.05 may be omitted. The ordered list may include second order Zernike function, Coma, Trefoil and secondary astigmatism.

The optical instrument may further include an input device for the patient or for an examination administrator or both. The image source may include a plane wave light source including substantially a point light source as a viewing target. A quality vision marker (QVM) may include one or more display items including one or more lines, one or more circles, one or more points disposed along a pattern of one or more lines or circles, or combinations thereof. The marker may provide a display pattern including one or more rings and/or parallel lines. A reference marker may provide a sweep line overlapping at the image source and having an orientation which is adjustable using the at least one input device until the patient indicates that the sweep line is aligned with a sharper linear image of the image source. Axis angle data of astigmatism errors of the patient's eye may be thereby provided.

The image source may include a plane wave point source placed two meters or farther away from the patient and having a diameter of two millimeters or less, or a substantially collimated light beam from a laser source that simulates a point source positioned two meters or farther away from the patient. An additional lens may be disposed to cause the image source to appear to the patient to be two meters or farther away. Spectral contents of the image source may include white light, substantially blue light, substantially yellow light, or substantially red light.

One or more spectacle, contact or intraocular lenses may have a prescription based on measurements by the optical instrument described herein.

A defocus power of the DCA and ACA may be adjusted within predetermined limits, including:

(i) searching for a residual line image of the point light source along the sweep line orientation;

(ii) reducing a diopter power of the DCA to attain a least minus power and at which a sharp line image is formed at the point source; and (iii) increasing ACA diopter power to reduce the line image to a small and substantially round point image.

The defocus power of the DCA and ACA may be differently adjusted within predetermined limits, including:

(i) searching for a residual line image of the point light source perpendicular to the sweep line orientation;

(ii) reducing diopter power of the DCA to attain the least minus power and at which a sharp line image is formed at the point source; and (iii) decreasing ACA diopter power to reduce the line image to a small and substantially round point image.

A display may be provided as a second viewing target centered approximately at the location of the point light source. The display may provide one or more viewing items including a sweep line. An orientation of the sweep line may be adjusted until the patient indicates that the sweep line has become substantially aligned with an orientation of the line image of the point source.

The optical assembly may include an astigmatism corrector assembly (ACA) including a pair of astigmatism wave plates, and the adjusting may include rotating an optical axis of the ACA to an orientation substantially perpendicular to the orientation of the sweep line. An amplitude of astigmatism correction may be increased by changing a subtended angle of the astigmatism wave plates until the line image of the point is reduced to a substantially round image.

One or more corrective lenses is/are also provided having a prescription generated by the subjective refraction method set forth above and/or below herein.

A further subjective refraction method is provided for generating a prescription for one or more corrective lenses. A collimated light beam is provided including substantially plane wave wavefronts. The plane wave wavefronts are projected into a patient's eye. An image of the wavefronts is formed at the patient's retina through an optical assembly in the light path including a defocus corrector assembly (DCA) or astigmatism corrector assembly (ACA), or both. The image initially includes refractive errors or optical aberrations, or both, of the patient's eye. While subjectively observing a shape of the image, the patient is instructed to search for and indicate at least one end point by adjusting the DCA or the ACA, or both. A prescription is determined for a corrective lens for the patient's eye based on known parameters of the optical assembly and on the adjusting of the DCA or the ACA, or both.

The at least one end point may include a line image which is observed by the patient to be at its sharpest or at its longest, or both.

A subjective refraction method for revising a prescription for one or more corrective lenses to correct higher order aberrations (HOA) of the eye of a patient is also provided. A point light source including substantially collimated plane wave wavefronts is provided at the patient's eye as a first viewing target. A low order prescription is input to a defocus corrector assembly (DCA) and an astigmatism corrector assembly (ACA) that are disposed along an optical path between the point light source and the eye of the patient, including setting an optical axis of the ACA to a cylindrical axis of the low order prescription. A brightness of the light source is adjusted to avoid eye saturation. The patient is instructed to observe one or more higher order aberration features around a point image of the plane wave. An angle of the optical axis or the power of the ACA or the power of the DCA, or combinations thereof, are adjusted to reduce the one or more higher order aberration features around the point source image.

The prescription is revised based on known parameters of the ACA or DCA or both and on the adjusting.

The size or the dimensions of the point source may be controlled or adjusted to provide high acuity vision of better than 20/15. A display may be provided as a second viewing target. The display may provide one or more rings centered approximately at the location of the point light source, or multiple circles, one line or multiple lines, a single point source, or multiple point sources arranged along one or more lines or circles, or combinations thereof. The diameter of at least one ring may be adjusted to provide a reference marker for the extent of the HOA. The brightness of one or more point sources or a size of one or more point sources, or both, may also be adjusted.

A subjective refraction apparatus is also provided for generating a prescription for one or more corrective lenses of a patient. A plane wave light source includes substantially a point light source as a viewing target. At least one input device is provided for the patient or for an examination administrator or both. An optical system is disposed along an optical axis between the point light source and the patient's eye which initially forms a blurry image of the point light source at the patient's eye. The optical system includes a defocus corrector assembly (DCA) including a fixed lens and a lens that is movable along the optical axis using the at least one input device for adjusting defocus power until the patient indicates that the blurry image has become a relatively sharp line image. An astigmatism corrector assembly (ACA) includes a pair of astigmatism wave plates that are relatively adjustable along its z-axis (perpendicular to the wave plate surface). One may use the at least one input device for adjusting the DCA or the ACA, or both, for astigmatism power or axis angle, or both, until the patient indicates that the line image has become a substantially round image.

A reference marker provides a sweep line overlapping at the point source and having an orientation which is adjustable using the at least one input device until the patient indicates that the sweep line is aligned with the sharp line image of the point source, thereby providing axis angle data of astigmatism errors of the patient's eye.

The plane wave light source may include a point source placed two meters or farther away from the patient and may have a diameter of two millimeters or less. The plane wave light source may include a substantially collimated light beam from a laser source that simulates a point source positioned two meters or farther away from the patient. A lens may cause an image of the point source to appear to the patient to be two meters or farther away.

Spectral contents of the light source may include white light, substantially blue light, substantially yellow light, or substantially red light.

The marker may provide a display pattern including one or more rings or parallel lines, a circle or multiple circles, one line or multiple lines, a single point source or multiple point sources arranged along one or more lines or circles, or combinations thereof.

Electrical or electronics hardware or computer programs, or combinations thereof, may be provided that perform individually or collectively one or more of the following tasks:

(i) drive movement of one or more optical elements in the DCA or ACA, or both, to change defocus or astigmatism power, or both;

(ii) display a location of an optical element;

(iii) convert a location or orientation reading, or both, to a refractive power in units of diopters;

(iv) collect data relating to adjustments to the DCA and ACA;

(v) set limits of movement range for the DCA or ACA or both to avoid over-correction;

(vi) automatically advance DCA or ACA refractive power, or both, when such task is requested; or (vii) automatic align the ACA optical axis when such task is requested, or combinations thereof.

DETAILED DESCRIPTION OF PREFERRED AND ALTERNATIVE EMBODIMENTS

Figure 1A:
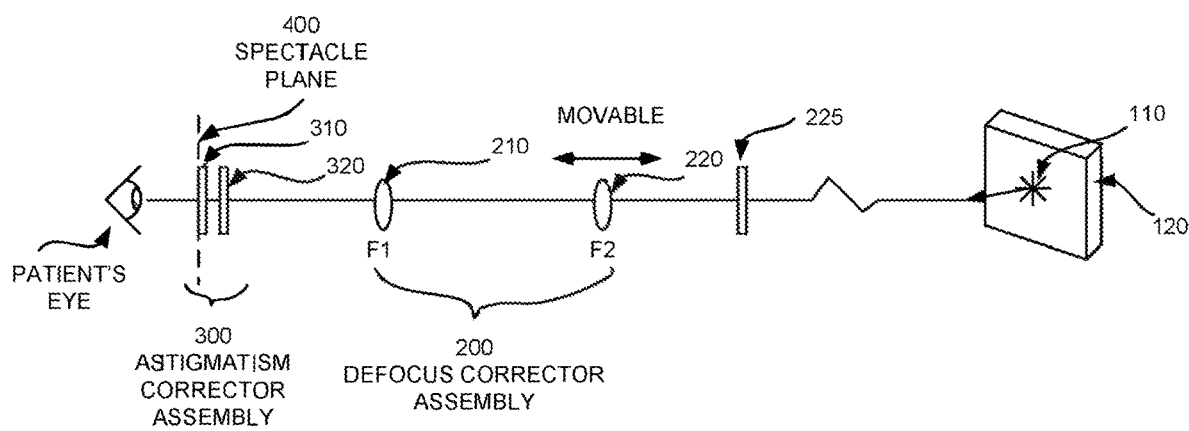
FIG. 1A illustrates subjective refraction apparatus in accordance with an embodiment.

In the entire specification, the term "wavefront refraction" shall be broadly construed to include any process of providing wavefront compensation to a patient's eye, while the patient is looking at a target. A "wavefront refractor" is a device which an eye care professional may use to perform refraction that includes correcting higher order aberrations of the eye, or sometimes referred to as higher order refractive errors. The "+/−" is also used herein before the second index of Zernike functions to represent a grouping of the pair of Zernike polynomials that have a same first index, wherein the second index has opposite sign. For example, the pair of Trefoil, $Z(3,-3)$ and $Z(3,3)$ are to be paired, and $Z(3,+/-3)$ shall designate a combination of the two Trefoils in an adjustable wave plate configuration. The term wave plate shall mean an optical plate that has the property of inducing an optical path difference profile. When a light wave passes the plate, the spatial profile across the two dimensions of the plate surface has a change in its wavefront in accordance with the optical path difference profile. A Zernike wave plate shall mean the optical path difference has a cross sectional profile as that of a Zernike function profile. The optical axis of a Zernike function may be assigned in accordance with a major symmetry axis of the Zernike function. For example the optical axis of $Z(2,+/-2)$ can be chosen either at zero degree or 90 degrees, and in this case selected according to an assignment of cylindrical cylinder lens axis.

Construction of Continuously Adjustable Zernike Function Wave Plates

The Zernike function wave plates described in the following can be manufactured using high precision free form diamond turning CNC machine, which is commercially available from Schneider, Germany. We adapt the Optical Society of America (OSA) convention for the Zernike functions, but omit the normalization constant for convenience. Using the trefoils as an example, and adding an amplitude and angular notation in the Zernike function designation. Two Zernike functions of Trefoil both having an amplitude of unity, and at an angle θ, are expressed as:

$$Z(3,-3,1,\theta)=\rho^3 \sin(3\theta)$$

$$Z(3,+3,1,\theta)=\rho^3 \cos(3\theta)$$

Note that: $Z(3,-3, 1, \theta)=Z(3,+3, 1, \theta+90/3)$, namely, the two trefoils in the Zernike polynomial functions are in fact identical except for an angular offset of 30 degrees. Suppose that one desires to have a variable wave plate of trefoil with variable amplitude ranging from 0 to 5. One first fabricates two identical Trefoil wave plates each with an amplitude of 2.5:

$$Z(3,-3,2.5,\theta)=2.5\rho^3 \sin(3\theta).$$

One achieves a total cancellation if one rotates one trefoil in the pair by 30 degrees relative to the second trefoil.

$$Z(3,-3,2.5,\theta+30)=2.5\rho^3 \sin(3(\theta+30))=-2.5\rho^3 \sin(3\theta)$$

$$Z(3,-3,2.5,\theta)+Z(3,-3,2.5,\theta+30)=Z(3,-3,2.5,\theta)-Z(3,+3,2.5,\theta)=0$$

When two identical Trefoils are aligned:

$$Z(3,-3,2.5,\theta)+Z(3,-3,2.5,\theta)=Z(3,-3,5,\theta).$$

Now, one can vary the Trefoil pair to any amplitude value, between 0 and 5, by rotating one or the other. It is preferable to rotate the pair simultaneously in identical angle, or approximately, but in opposite direction. That way, the optical axis of the combined wave plate assembly remains stationary, while the amplitude is adjusted.

The sum amplitude of 5 from a pair of plates with amplitude of 2.5 is used merely as an example for illustration. No limitation is to be inferred on the range of the amplitude of the Zernike wave plate assembly using a technique in accordance with a preferred embodiment.

Likewise, one can construct continuously adjustable Coma wave plates by substantially following the above steps, except replacing the Zernike function designation from a Trefoil to a Coma designation, basically by replacing the second index +/−3, inside the bracket, with +/−1.

For the fourth order Zernike terms, like tetrafoils $Z(4,+/-4, 1, \theta)$, the method described above also applies. In this case, the continuously adjustable device comprises two tetrafoil wave plates of equal amplitude. However, the total cancellation, or the zero tetrafoil, occurs when the relative angle θ is at 90/4, or 22.5 degrees. Moreover, the technique of this preferred embodiment may also be used to construct continuously adjustable secondary-tetrafoils $Z(4,+/-2, 1, \theta)$, because the angular part of the secondary-tetrafoil is identical to the those of tetrafoils.

Zernike functions other than those with a zero in the second index, such as $Z(4,0)$, $Z(6,0)$, etc., can be paired off (those terms that have almost identical designation, except for a plus/minus sign difference in the second index in their functional representation), and a continuously adjustable device can be constructed using the technique provided above.

The Visual Significance of Symmetric Zernike Functions and their Correction

Concerning the Zernike terms of fourth order and higher, and having a second index of zero, the following three points are noted. First, these terms are symmetric in nature, while irregularly shaped corneas that cause serious visual symptoms and complaints such as keratoconus are seldom rotationally symmetric. Second, the point spread function resulting from these aberration terms have a tight focus, but with some halo effect at nighttime around bright light sources. The visual acuity is not so affected during daytime, but the contrast sensitivity would suffer to some extent. Third, and fortunately, the defocus term Z(2,0) can be used effectively to counteract these aberrations, canceling most, if not all, of the aberration from these fourth order and higher Zernike terms. Therefore, the compromise on the quality of vision may be made small and even negligible by not having a continuously adjustable symmetric wave plate for Z(4,0), Z(6.0) and those of even higher order terms.

Subjective Wavefront Refractor Having Continuously Adjustable Zernike Function Wave Plates Previously, the same inventor has filed patent applications entitled, "Subjective wavefront refraction correcting low and high order aberrations", corresponding to US application Ser. Nos. 60/773,758 and 11/675,079, which are incorporated by reference in their entirety.

In these referenced applications, a subjective refraction device is described, which comprises two continuously adjustable assemblies, one for the defocus Z(2,0), and one for astigmatism Z(2,+/−2). Using the device and method according to the referenced applications, the second order terms correct a good portion of the high order aberrations. However, there will be residual HOA.

Quality Vision Marker (QVM)

Figure 1B:
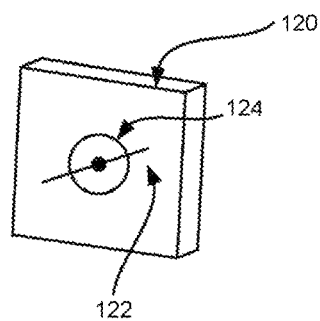
FIG. 1B illustrates a quality vision marker (QVM) including point light source in accordance with an embodiment.

Another component of the preferred refraction system is a Quality of Vision Marker (QVM), which is illustrated as 120 in FIG. 1(a). It includes a display (LCD monitor, for example) and a computer program that generates various display items. The QVM is useful to assist the patient to identify refraction error, including the identification of an axis of astigmatism. A monitor and some display items are illustrated in FIG. 1(b). One example of such display item is a radial sweep line with the center overlapping the point source. The sweep line 122 points from the origin of the coordinate, that is at the point source's location radially, or it can extend diametrically through the origin point, namely, when one arm of this line is pointing at 30 degrees, and the opposite end of the sweep is pointing at 210 degrees. A set of parallel lines can also be used in the sweep. The displayed items are typically overlapping with or proximate to the point light source.

Figure 1C:
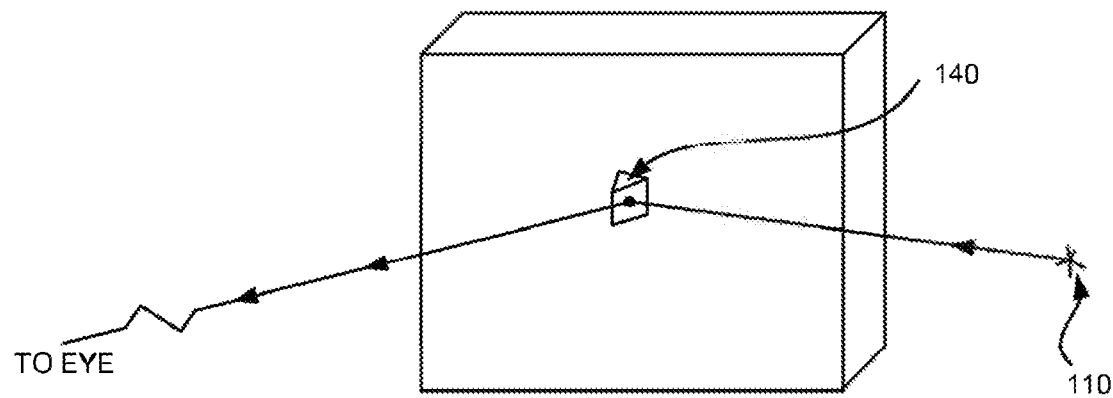
FIG. 1C illustrates a QVM with point light source reflected from the side in accordance with an alternative embodiment.

In Box 520, a Quality of Vision Marker (QVM), which includes a LCD monitor along with items of image displayed on it, may be either placed at the point source as shown in FIG. 1(a), with the point source substantially at the center of the monitor, thereby the radial sweep line originates at the point source, and the ring pattern is concentric to the point source as well. Alternatively, the point source may be detached from the monitor, and in the place of the point source in FIG. 1, at the center of the monitor is a 45-degree mirror 140, and the point source placed farther down as shown in FIG. 1(c). This layout has the advantage of wiring and the bulk associated with the point source will not interfere with the display on the QVM monitor.

Alternatively, the QVM monitor may be placed off the direct beam path of the point source in FIG. 1(a). With a 45-degree window that is semi-transparent, with a partial (50%, for example) transmission, in the beam path and establishes a second path of the patient's line of sight towards the monitor, such that the patient sees both the QVM monitor and the point source target. This layout also eliminates blockings that may be caused by the wires of the point source.

In FIG. 1(a), a patient's eye is shown to look along the beam path of the point source, and the QVM monitor. The patient's head is properly restrained, with a headband (or a headrest) and a chin rest. Other method of keeping the head/eye position steady may also be used.

The QVM is also capable of generating rings, 124, which center at the point source, and whose radius can be varied with an input control. It also generates parallel lines, or any other display items that can enable patient communication with the examiner on the status of the patient's eye conditions. The QVM device can be a round disc with a straight line passing through the center. In this case, the disc is rotatable with respect to its center. Concentric markings and other parallel line marking are also provided. Light channels are provided to feed illumination light to the diagonal line, or lines, parallel lines or the rings, so that only the desired item is lighted for the patient. A subjective wavefront refraction method is described below detailing exemplary methods for using the QVM to estimate astigmatism axis error.

The intensity levels and the size or the dimensions of the point source, and those of the display items of the QVM are adjustable; via some touch keys, infrared or blue-tooth removal control, or other control means.

Figure 1D:
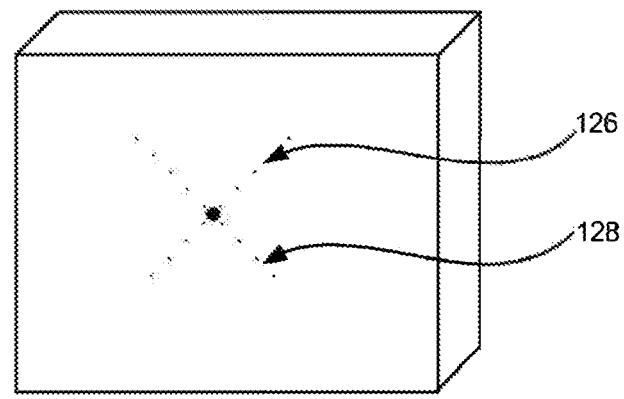
FIG. 1D illustrates a QVM with series of points arranged in two lines as display items around the point light source in accordance with an embodiment.

In an embodiment, multiple point sources may be presented. They can be physically focused spots or spots constructed to display in a LCD or DLP monitor. In FIG. 1(d) multiple points are constructed along a sweep line 126, instead of a solid sweep line as in FIG. 1(b), 122. Furthermore, multiple sweep lines can also be presented as shown in FIG. 1(d), 126 and 128. As will be shown later, it is advantageous to arrange the sweep points 126 and 128 at 90 degrees. However, the angle of separation among the multiple lines sweeps may be at angles other than 90 degrees.

Figure 1E:
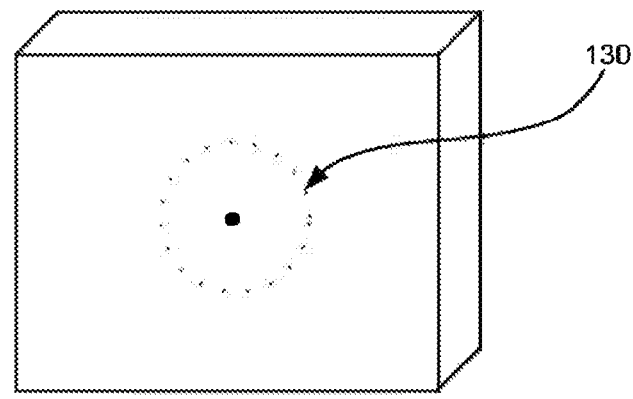
FIG. 1E illustrates a QVM with a series of points arranged in a circle as display items around the point light source in accordance with an embodiment.

In another embodiment, the multiple point sources may be arranged in a circle 130, as shown in FIG. 1(e). Multiple circles are optional. In addition to the patterns described above, points and lines can be arranged to form other patterns such as squares, ellipses, rectangles, other polygons such as triangles, or parallelepipeds. The spot size, its brightness and spots separation distance in lines 126, 128 or circle 130, or other patterns are adjustable to suit the purpose for the refraction procedures.

The refraction device also provides fixation for the patient's head. It may include a headband, a headrest, and/or chin rest, similar to those in most slip-lamp instruments, providing a rest position for patient's head and eye. Other method of keeping the head stationary may include a bite bar. Once the head position is stationary, the spectacle plane 400 of the eye is now known relative to the eye, which is about 12-15 mm from the apex of the patient's eye.

Defocus Corrector Assembly (DCA)

After the patient has kept his head stationary as described, the refraction starts with determining the defocus refractive errors. Defocus Corrector Assembly 200 is capable of providing a continuously variable power change at the spectacle plane of the patient's eye under examination. This is in contrast with the discrete incremental power change in a phoropter typically in 0.25 diopters steps. The present refraction method and device may include multiple or a series of lenses in smaller diopter power increments to be inserted in place of the DCA to accomplish the advantageous objective of finding the optimal refraction for the patient. For example, an instrument including lenses in 0.125 diopters increments, or in 0.0625 diopter increments may be used.

In the example illustrated at FIG. 1(a), the optical elements in the Defocus Corrector Assembly preferably include a pair of achromatic lenses 210, 220. Lens 210 has a focal lens F1, with a back focal length at the spectacle plane 410, and its position is preferably stationary. A second lens 220, has a focal length F2, and is positioned along the optical path of the patient's line of sight to the point source 110. Lens 220 is movable along the optical axis along the line of sight of the patient's view of the target point source. Depending on the location of lens 220 relative to lens 210, the Defocus Corrector Assembly produces either plus or minus lens powers at the patient's spectacle plane 400. The preferred range of defocus refractive power change is from +10 diopters to −12 diopters, and the range can be extended to +12 diopters to −20 diopters, or larger dioptric range if one desires. Alternatively, a series of spherical lenses may be used.

In one embodiment, the DCA is designed to optimize its field of view and minimize optical distortion on axis and off axis. The variable diopter range may be, for example, +8 D to −10 D. One may extend the useful diopter range of the instrument by placing a single additional lens at the patient's spectacle plane. In one example, so placing a +8 D lens, the patient can be refracted up to an extended range of +16 D. Likewise one may extend the minus diopter range to −20 D with the insertion of one −10 D lens at the patient's spectacle plane. The extension method places no limitation on the field of view and substantially reduces the design requirement in the optics, demanding +18 D to −20 D all provided by lenses 210 and 220.

Astigmatism Corrector Assembly (ACA)

The astigmatism of the eye is preferably determined by using an Astigmatism Corrector Assembly 300, including pure astigmatism wave plate optical elements positioned near the spectacle plane of the patient. By pure astigmatism, it is meant the wavefront correction is to be described by either the Zernike functions Z(2,2), Z(2,−2) or combination thereof. Here and in the following, symbols of Zernike representation are used as adopted by the Optical Society of America, as described in Appendix one of "Customized Corneal Ablation: Quest for Super Vision" edited by MacRae, Krueger and Applegate, published by Slack in 2001, which is hereby incorporated by reference. Alternatively, it can also be positioned at an equivalent spectacle plane, which is produced by a relay lens system which may include a pair of lenses positioned at focal length separations from each other to produce a conjugated spectacle plane. The ACA is capable of providing continuously variable, pure astigmatism correction of the Zernike terms Z(2,2) and Z(2,−2). The astigmatism wave plate can be manufactured using CNC machining in an optical quality plastic plate or other type of substrates. Each of the optical elements are machined to provide an optical path difference (OPD) according to the shape of a Z(2,2) or Z(2,−2). This is an advantageous feature of the preferred refraction device. The preferred device goes beyond using cylindrical lenses mounted in a wheel. Cylindrical lens power also includes a component of defocus. Therefore, arriving at a final reading using cylindrical lenses involves adjusting a corresponding compensational change in the sphere component. This process can be tedious and can encourage accommodation and hence over-correction.

Using a modified notation of the Zernike Polynomials (without the normalization coefficients): $Z(2,+2, \theta) = r^2 \cos(2\theta)$ (1) And $Z(2,-2, \theta) = r^2 \sin(2\theta) = r^2 \cos(90 - 2\theta) = Z(2,+2, \theta - 45 \text{ degree})$.(2) where the third index within the bracket of the Zernike function designates the rotational angle of the astigmatism wave plate. Indeed Z(2,2) and Z(2,−2) terms are physically identical, except for the orientation of its optical axis being rotated by 45 degrees. If one desires an astigmatism correction range of 0 to 6 diopters, for example, the Astigmatism Corrector Assembly (ACA) may include two identical 3 diopter pure astigmatism wave plates. In the following it is shown that when these two plates have their axes aligned, it produces the maximum effect of 6 diopters of pure astigmatism, and when the angle subtended by the axes is 90 degrees relative to each other, it produces a total cancellation of each other's effect. Therefore, one may vary the amplitude of pure astigmatism by setting the angle subtended by the optical axes of two identical astigmatism wave plates: Variable $Z(2,+/-2) = Z(2,+2, \theta+\phi) + Z(2,+2, \theta-\phi)$ (3)

Where angle $\phi$ is the subtended angle of each of the wave plate respect to initial axis combined unit ACA, therefore the total subtended angle between the two wave plates is $2\phi$. The initial axis of the combined unit is chosen to be at 90 degrees, since Z(2,+2) generates a negative cylinder lens at 90 degrees when a negative power sphere of half of its amplitude is added to it. Starting with two Z(2,2) wave plates, optically aligned, one has the maximum astigmatism effects of 2Z(2,2).

Now one starts counter rotating the identical plates with an equal angle $\phi$, $Z(2,+2, \theta+\phi) + Z(2,+2, \theta-\phi) = 2Z(2,+2, \theta)\cos(2\phi)$ (4)

Therefore, maximum effect is at $\phi$ equal to zero, namely two plates are optically aligned, and minimum at $\phi$ equal 45 degrees. In this case, one can choose the optical axis of the combined unit to be at 90 degrees. Regardless of the value of counter rotating angles, the optical axis remains unchanged, the negative cylinder lens of equation (4) remains at 90 degrees when an appropriate amount of negative sphere is added to the combined unit. In application, one marks the 90 degree orientation as the optical axis of the combined unit in Equation (4), and the amplitude of the astigmatism decreases with increasing angles of $\phi$. To provide another illustration, one may choose to start with two identical pure astigmatism wave plates that totally cancel each other instead of reinforcing each other as in the example above. The identical plates are rotated relative to each other by 90 degrees: $Z(2,+2, \theta) + Z(2,+2, \theta+/-90) = Z(2,+2, \theta) - Z(2,+2, \theta)$ (5)

This is identical to zero at any $\theta$. The amplitude of the two wave plates are counter-rotated by angle $\phi$: Z function $(2, +2, \theta+\phi) + Z$ function $(2, +2, \theta-\phi) = -2 \sin(2\theta)\sin(2\phi)$ (6) $= -2 Z \text{ function}(2, -2, \theta)\sin(2\phi)$ (7)

In this case, the maximum amplitude of pure astigmatism is obtainable when counter rotational angle $\phi$ is at 45 degrees, or when the two plates are 90 degrees relative to each other. The maximum amplitude is achieved at counter rotational angle $\phi$ at 45 degrees where the amplitude of the ACA is the sum of the two wave plates. However, the resultant wave plate has wavefront profile of Z(2,−2) even though one starts out with two identical Z(2,2) plates. What this means is that variable amplitude pure astigmatism may be aligned along −45 degree angle relative to the starting orientation axis direction as defined by the two identical wave plates. This can be made understood using Equation (2) with Equation (7). Therefore, the power or the amplitude of the astigmatism is adjustable by controlling an angle between the axes of the two astigmatism wave plates. In a preferred embodiment, the negative cylinder axis of the Z(2,−2) is to be marked as the optical axis of the combined wave plate unit. In application, if the two starting wave plates were aligned to produce a net astigmatism of zero, or plano, as shown in Equation (5), after a counter rotation .phi. of the combined unit, the net optical axis of the astigmatism is at 45 degrees. It will produce a negative cylinder lens effect upon adding a negative power sphere lens at half of the astigmatism amplitude to the combined wave plate unit. When referring to an increase of astigmatism amplitude, one may achieve it by increasing the angle .phi., so that a negative cylinder condition of an eye is reduced or neutralized. As an example, a negative cylinder notation with axis at zero degrees can be produced with a wave plate having a wavefront correction profile of −Z(2,2, .theta.) plus an appropriate amount of negative power sphere Z(2,0).

The present refraction method and device may include multiple or a series of cylindrical lenses in smaller diopter power increments to be inserted in place of the ACA to accomplish the advantageous objective of finding the optimal refraction for the patient. For example, an instrument including lenses in 0.125 diopters increments, or in 0.0625 diopter increments may be used.

Sign Convention for the Cylinder Lenses

A final prescription generated based upon the exemplary refraction procedure preferably has a minus cylinder notation. A negative cylinder notation may be converted to a plus cylinder notation in a spectacle prescription, which indeed specifies the same eyeglasses therefore, produces the same effects for refractive error correction. The instructions as described hereunder can be modified to arrive at a positive cylinder prescription. In that event, instead of finding the end point at a negative cylinder focal plane where the plane wave has an image of a sharp line, one would search for a sharp line image at the positive cylinder focal plane. One would also make corresponding modifications in the refraction procedure to accomplish the respective goals.

High Order Zernike Wave Plates in a Wavefront Refractor

Instead of positioning the Zernike wave plates right next to the patient's eye, which would be crowded, the wave plates may be advantageously positioned in accordance with another embodiment at the equivalent pupil plane (refer to FIG. 1, element 225 is a plane where the wave plates are located) after the Defocus Corrector Assembly 200, or IDCA 200 in FIG. 1. FIG. 1(a) of U.S. application Ser. No. 60/773,758 is incorporated into the present specification as FIG. 1 for illustration. A wave plate can be any of a variety of optical devices that have a distribution of optical path differences across their transverse extent relative to the optical path within which they are positioned. A lens and a curved mirror are examples. A lens may be rotationally symmetric, but in the case of a trefoil, e.g., it is not. A wave plate is any reflective or transmissive optic corresponding to a selected Zernike function. For example, another wave plate is a coma wave plate. A wave plate assembly in accordance with a preferred embodiment includes at least two wave plates that can be relatively displaced to change optical amplitude or angle or both.

FIG. 1 schematically illustrates the optical layout of a device in accordance with a preferred embodiment. A conjugate pupil plane 225 of the patient's eye under examination is located at approximately the focal point 225 of the lens f2, 220 in FIG. 1, between the lens f2 220 and the target 110. The target is located ideally for positioning a pupil limiting aperture or pinhole as discussed in the referenced application. Preferably, the wave plate assembly that is located at plane 225 is also mounted on a same movable platform as the lens f2 (220) is mounted on. Thereby, the distance between lens f2 (220) and the wave plate assembly that is located at plane 225 remains the same when lens 2 (220) is moved to provide an adjustable defocus diopter power.

Processes which Utilize the Wavefront Refractor Overcoming the Patient Selection Problem of Objective Wavefront Refraction Methods One drawback of the objective method of refracting a patient is the lack of patient feedback. Until now, commercial wavefront aberrators have been limited to measuring optical aberrations of the eye. Some have attempted to correct aberration by canceling it by way of incorporating an exact opposite of the wavefront error profile in spectacles or contact lenses. Ideally, if all the optics are aligned properly, the resulting image that forms at the retina of the patient would be diffraction limited. One remaining issue is that the patient may not appreciate the difference of the high order wavefront corrected image compared to that corrected with the second order, namely, sphere, cylinder and axis.

Therefore in accordance with certain embodiments, a measured total order wavefront error is input into the wavefront refractor. Communicating with the wavefront refractor is a computer running a computer program coupled to control the drive mechanism. The computer is preferably used to control the movement of the optical components including the defocus corrector assembly 200 including lens f1 (210) and lens f2 (220), the astigmatism assembly 300 including optics 310 and 320 shown at the spectacle plane 400 in FIG. 1, and the high order Zernike function wave plates located at plane 225 in FIG. 1, setting them to cancel the patient's wavefront error. Now, the patient looks through correction optics, including the low order optics 200, 300, and the high order wave plates at location 225, and looks at a viewing target such as a nearly collimated light beam, a small point source, real physical objects, a high definition image from a monitor, or an image from film, or a combination thereof. The patient can then decide if the high order correction does make a difference, and make a decision on the purchase of just regular eyeglasses or contact lenses, or instead pay a premium for a wavefront corrected device in accordance with a preferred embodiment. A device in accordance with a preferred embodiment eliminates uncertainty involved in "patient selection". Without the subject patient participation, objective wavefront refraction inherently involves a prior patient selection algorithm. Since no algorithm can reliably read a patient's mind, such would quite likely select the wrong candidate from time to time, with negative consequences involving patient complaints and demands for a refund of the purchase amount.

Subjective Wavefront Refraction with Patient Participation

In another embodiment, a patient subjectively adjusts wave plates, e.g., located at plane 225 in FIG. 1, to achieve optimized vision. One may use a device in accordance with a preferred embodiment to generate an HOA wavefront by selecting a combination of the Zernike function wave plates, in selected amplitudes and angles. In addition, the wave plates may comprise substantially all Zernike functions, while the patient's vision is being tested. Also, the patient can now subjectively determine an improvement in vision quality by adding/subtracting a Zernike function wave plate, and/or changing the amplitude and the angle of a Zernike function.

Forming an Ordered List of Decreasing Significance of Zernike Functions

It is recognized by the present inventor that there is great significance in establishing a procedure that leads to a final refraction point.

In one embodiment, a list is established for Zernike functions in an order of decreasing significance, and uses this ordered list to guide the patient to find the end point of subjective wavefront refraction. Here, the Zernike functions are paired with the same first index, and the second index has the numeral except in opposite sign. Trefbils may be used as an example. It was shown above that the two trefoils are in fact identical in profile except for a relative rotation of 30 degrees. Henceforth, +/−notation is used in the second index of a Zernike function to denote pairing of two Trefoil functions.

$$Z(3,+/-3,a,\varphi)=Z(3,-3,b,\theta)+Z(3,+3,c,\theta),$$

where "a" represents the resulting amplitude after combining the two trefoils with amplitude "b" and "c", and the angle φ is the angle of orientation of the optical axis of the resulting trefoil.

In one embodiment, defocus Z(2,0) is given the top position in the ordered list, followed by astigmatism (amplitude and angle). In the following, an exemplary ordered list of Zernike functions is provided in the OSA designation, and/or a modified OSA designation with the Zernike pairing schemes as proposed in an earlier paragraph:
  1. Z(2,0)
  2. Z(2,+/−2)
  3. Z(3,+/−1)
  4. Z(3,+/−3)
  5. Z(4,+/−2)
  6. Z(5,+/−1)
  7. Z(4,+/−4)
  8. Z(5,+/−3)
  9. Z(6,+/−2)
  10. Z(6,+/−4)
  11. Z(5,+/−5)
  12. . . . .

The amplitude distribution of Zernike functions in normal human eyes drops rapidly after the fourth order terms (OSA), and second order terms are ordinarily the most prominent. The ordered list above may continue with more terms. However, the contribution of the remaining terms is expected to be small, except in cases of keratoconus eyes and those after corneal transplant surgery or traumatization, or the like. The exact ordering of the Zernike components in the list is not a limitation to the invention or embodiments thereof. In another embodiment, the placement of terms of the Zernike function in the ordered list is modified according to clinical experience learned from patient feedback when the method is used in clinical practice over time. Thereafter, a modified ordered list is to be established, or customized for a particular situation with the patient, whether the eye has keratoconus conditions or post corneal transplant.

In another embodiment, if a patient's wavefront error has been measured with a subjective wavefront aberrometer, it would be clear that certain Zernike terms are more dominant and some Zernike terms such as coma or trefoil are small or missing altogether. The small Zernike terms, with RMS amplitude of less than 0.03 microns can be skipped over from the ordered list, during the subjective wavefront refraction process. In another embodiment, the Zernike function is ordered in accordance with the RMS amplitude of the patient's wavefront errors, and the most dominant Zernike term gets moved up the list, and is followed by the next highest amplitude term, and so on.

Subjective Wavefront Refraction Procedure

In the previous U.S. application Ser. Nos. 60/773,758 and 11/675,079, detailed procedures have been given to achieve optimized values for low order Zernike terms, Z(2,0) and Z(2,+/−2), traditionally called the defocus and astigmatism and axis angle. In the optimization process, the refractive errors relating to defocus and astigmatism is substantially reduced. One advantageous aspect of this refraction method is in each element of the process, there is a distinct end point for the patient to search for. Therefore, each element may be achieved without confusion. What follows are exemplary end points for arriving at optimal prescriptions for eyeglasses, or contact lenses. The prescription may also be used for refractive surgery. Distinct end points may include:
  1. Without correction, a patient would typically see a diffuse image of a point source viewing target. First, defocus refractive error is substantially removed by continuously adding or subtracting refractive power using the DCA device, until a relative sharp line image, or an otherwise elongated image, is formed from the point source target.
  2. To correct for the astigmatism, the ACA device is adjusted to turn the line, or elongated image, and/or condense it into a substantially round image.
  3. Next, the defocus power is increased or decreased, depending on whether the refraction is for a positive or negative cylinder convention, and the round image is condensed into substantially a point image.
  4. For correction of a higher order aberration, greater than the second order Zernike aberrations, one attempt to reduce star bursts around a point image may be achieved in (3) above. The defocus and astigmatism may be further adjusted. Moreover, adjustments may be added with other higher order wave plates such as coma and trefoil. Third and higher order Zernike function wave plates may be used to further tighten the point image into a sharp point substantially free of star bursts.

In certain embodiments, one Zernike wave plate assembly is tested at a time. A point source, or multiple point sources as described in 60/773,758 and Ser. No. 11/675,079, may be presented to the patient as the viewing target. As in the previous disclosure, the points, or substantially the points may be arranged in a certain predetermined pattern to facilitate and improve test speed and accuracy. In testing a wave plate of third order or higher in Zernike function, the end point to be searched by a patient undergoing an eye examination is to achieve a sharpest focused point image of the point or points at the viewing target.

In accordance with an embodiment, after the low order Zernike terms have been determined, one selects the next Zernike function term from an ordered list. The list illustrated above under the heading, "Forming an Ordered List of Decreasing Significance of Zernike Functions", or a modified, abridged or expanded list, can then be used as a default list. Some re-arrangement may be derived from evidenced success from clinical feedbacks, as discussed. Assuming that clinical data confirms the significance ordering of Zernike functions in the list above, then as an example, and without inferring any limitation, the next most significant Zernike function can then be selected, which in this example is Z(3,+/−1), known as the "Coma". One may first increase the amplitude as an example, in 0.05 micron increments, and between each incremental step, the patient may rotate the coma assembly axis angle to find the best angular position. Again, a substantially collimated light source is preferably used as our viewing target for the high order wavefront refraction procedure. Alternatively, a small point source positioned sufficiently far away from the patient can also be used. The importance and the usefulness of using such a target has been discussed in the U.S. application Ser. Nos. 60/773,758 and 11/675,079 which have already been incorporated by reference. It offers sufficient sensitivity for finding a final refraction end point. The end point for the patient to search for is the tightest point image with least amount of star bursts. The star bursts are related and indicative of the existence of higher order aberrations of the vision of the patient.

Some steps of adjusting, back and forth between the amplitude and the angle change are expected. Preferably, the patient has one hand on one knob controlling the amplitude, and the other hand on a knob adjusting the angle. The process can move along quickly, such that these steps will not lead the patient to a state of confusion.

Once the end point for Coma is reached, the wave plate assembly is keyed up for the next Zernike function to be adjusted in a similar manner as is done for the Coma wave plate assembly. Once the end point of that Zernike function is reached, one moves on to the wave plate assembly of the next most significance Zernike function to present to the patient along his/her line of sight at the location as specified, and so forth.

If there is no perceived improvement in the quality of the image when it reaches a certain Zernike on the significance list, at say term number 7, Z(5,+/−1), Secondary Coma, as it is sometimes referred to, in our example shown in the last section, then the wavefront refraction procedure is preferably considered completed.

Even though the feature of being able to continuously vary the amplitude of the wave plate is a significant advantage, we place no limitation on applying all mentioned methods and test techniques to perform a vision improvement test with a series of wave plates having discrete increments in wave amplitude, in place of the continuous variable wave plate device as presented here. Such discrete plates may be mounted on a wheel, e.g., like those in a phoropter, and/or on translational stages to be moved in and out of the line of sight of the patient under test.

Detailed Mechanism for Continuous Adjustability in Wave Plate Assembly

Figure 2:
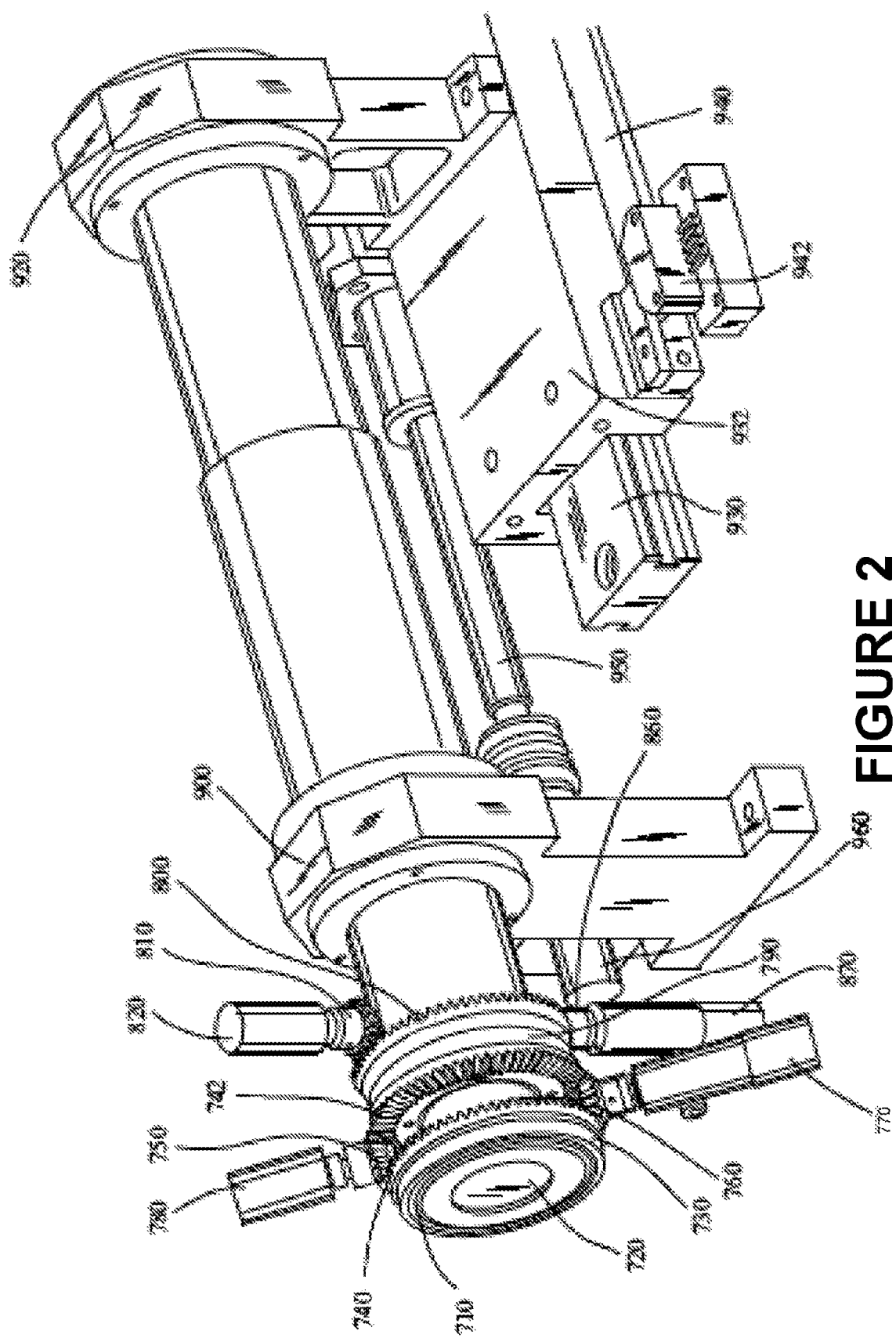
FIG. 2 schematically illustrates an optical instrument in accordance with an embodiment.

In accordance with another embodiment, a motorized mechanism is provided for a Zernike function wave plate assembly, which is applicable to any of the Zernike functions included in this specification. In a preferred embodiment, as illustrated at FIG. 2, a pair of Zernike wave plates are mounted on a rotary ball bearing. One of the wave plate pairs is shown, labeled 720, on bearing 710. Only one of the pair is shown. A view of the second ball bearing and of the second wave plate is blocked in FIG. 2, while the mounting and the motion mechanism is similar to that of the first wave plate. The inner ring of the ball bearing 710 is attached to a bevel gear 740. Similarly, the second wave plate is mounted with a second ball bearing, and the inner portion of the second ball bearing is attached to a second bevel gear 742.

In one embodiment, two pinion gears are used. One pinion gear 760 may be used to drive both bevel gears, as illustrated in FIG. 2, which in turn rotate the pair of wave plates in equal angles but in opposite direction. This counter rotating motion of the Zernike wave plate pair accomplishes the goal of adjusting the amplitude value of the combined wave plate assembly. As it is stated above, and in U.S. application Ser. Nos. 60/773,758 and 11/675,079, when two identical wave plates of a selected Zernike function are substantially aligned with overlapping optical axes, the paired wave plates generate the maximum wavefront amplitude. Using again the Trefoil example, if one uses two wave plates, each with amplitude of 2.5, the maximum amplitude achievable is the sum, or 5. As the relative angle between the wave plate pair increases, the overall amplitude of the assembly unit decreases, and the sum amplitude becomes zero when the optical axis of the two Trefoils are at 90/3, or 30 degrees apart. Therefore, an amplitude control ranges from zero to a maximum of 5. Other desirable adjustable ranges may be constructed similarly utilizing two identical wave plates each having half of a desired maximum.

A motor unit 770 illustrated in FIG. 2 is attached to a drive pinion gear 760. The motor unit 770 can include a DC motor, a step motor, or another suitable mechanism that turns the pinion gear 760. A second pinion gear 750 is also preferably mounted between the two bevel gears 740 and 742. This second pinion gear is used as a rotary angle sensing device and is attached to a rotary encoder 780. Electrical output is fed to an encoder reader which reads pulses and pulse edges. This information is converted to an angular position of the optical axis of each of the wave plates. A second computer program routine then calculates the sum amplitudes of the two wave plates, from the relative angular movement for a given amplitude of the individual wave plates. An overall amplitude of the wave plate pair is then displayed in a monitor, LED, LCD, or any suitable display device, including thermal printer.

Outer rings of ball bearings 730 and a corresponding outer ring for the second ball bearing are attached to inner rings of third and fourth ball bearings. The outer rings of the third and the fourth ball bearings are in turn supported and mounted to the base of the instrument (not shown). The outer ring of the fourth bearing 790 is shown in FIG. 2, but the view of its inner ring is obscured. That inner ring of the fourth ball bearing 790 is attached to a third bevel gear 800. The entire counter rotating unit of the first and second bearings are affixed to the inner ring of the fourth bearing 790, and a second motor 870 is connected to and drives the third pinion gear 860, which in turn rotates the entire counter rotating assembly comprising the first and second ball bearings and the counter rotating wave plates. A second rotary encoder 820 is attached to a fourth pinion gear 810 and senses an angular rotation of the entire counter rotating assembly, which is the angle φ, of the optical axis of the entire counter rotating wave plate pair. Again, the electrical output of the encoder 820 is fed to an encoder reader. A separate computer routine converts electrical pulses from the encoder into an angle reading, which is the angular orientation m, of the optical axis of the wave plate pair.

Alternate Method of Driving the Continuous Variation in Amplitude and Angle

Instead of using pinion gears to drive the two wave plates of the ACA, which are preferably substantially identical, in opposite direction, preferably at identical angular rates or otherwise in identical angular amounts per increment, one may use synchronized motor drives. In such construction, each wave plate is driven by its own driver electronics. However, two driver circuits are controlled by a closed loop algorithm, such that the two motors still move substantially in "lock-step", or move continuously or jog in steps, in substantially identical angle increments in the same or opposite directions, during any commanded movement. The motor movement is monitored by rotatory encoder. An amplitude precision greater than 0.01 diopters is in this way achievable in a 6 diopter astigmatism adjustable wave plate unit.

A Mechanical Design for a Wavefront Refractor

In the previous paragraph, an embodiment was described of a continuously adjustable wave front generation unit of a Zernike function of second order or higher, with non-zero second index (except Z(2, 0). The structure of this may be as described in the US application Ser. Nos. 60/773,758 and 11/675,079. Zernike function wave plates are not made with a symmetric generating machine with two axis grinding and polishing, such as those used to generate sphere and cylindrical surfaces in spectacle lenses. A high precision commercial 4-axis and 5-axis freeform generator machine can cut a surface profile and even polish along the contoured surface. One expects each of such custom-made wave plates would be much more costly. This is an advantage of the technique of certain embodiments which use only two wave plates to create infinite and variable amplitudes and angles, as compared to other embodiments that use a series of wave plates at fixed amplitude, and incremental amplitudes, similar to a series of lenses on a disk inside a phoropter. The former technique also overcomes the problem of requiring a large number of wave plates each with smaller increments in amplitude.

Indeed, FIG. 2 also represents an embodiment of a structural design of the optical layout of a wavefront refractor as described in U.S. application Ser. Nos. 60/773,758 and 11/675,079. That instrument could be manufactured with only two continuously adjustable Zernike functions, i.e., the astigmatism and the defocus. The astigmatism wave plate assembly (300 of FIG. 1) is shown on the left in FIG. 2, and is also referred to as an illustration of how other continuously adjustable wave plate assemblies may be constructed. The defocus assembly (200 in FIG. 1) includes two lenses f1 (210 of FIG. 1) and f2 (220 of FIG. 1), which are mounted in optics holders 910 and 920, respectively. The lens mount 920 is affixed on a linear slide 930, which is movable along the optical axis of the patient's line of sight. A linear encoder strip 940 is attached to the movable platform 932, and an encoder reader head 942, generates electrical pulses as the encoder strip travels across it. The encoder output is fed to a pulse counter, and a computer routine is used to covert the count into the location of lens f2 relative to f1, and it subsequently calculates the diopter power of the defocus assembly unit. The diopter reading is displayed preferably by a suitable method such as was mentioned in the case of the rotary encoder.

The movable platform of the linear slide is driven by a lead screw 950, which is turned by a motor 960. Any kind of motor with the desired speed, resolution and accuracy may be used.

Figure 3:
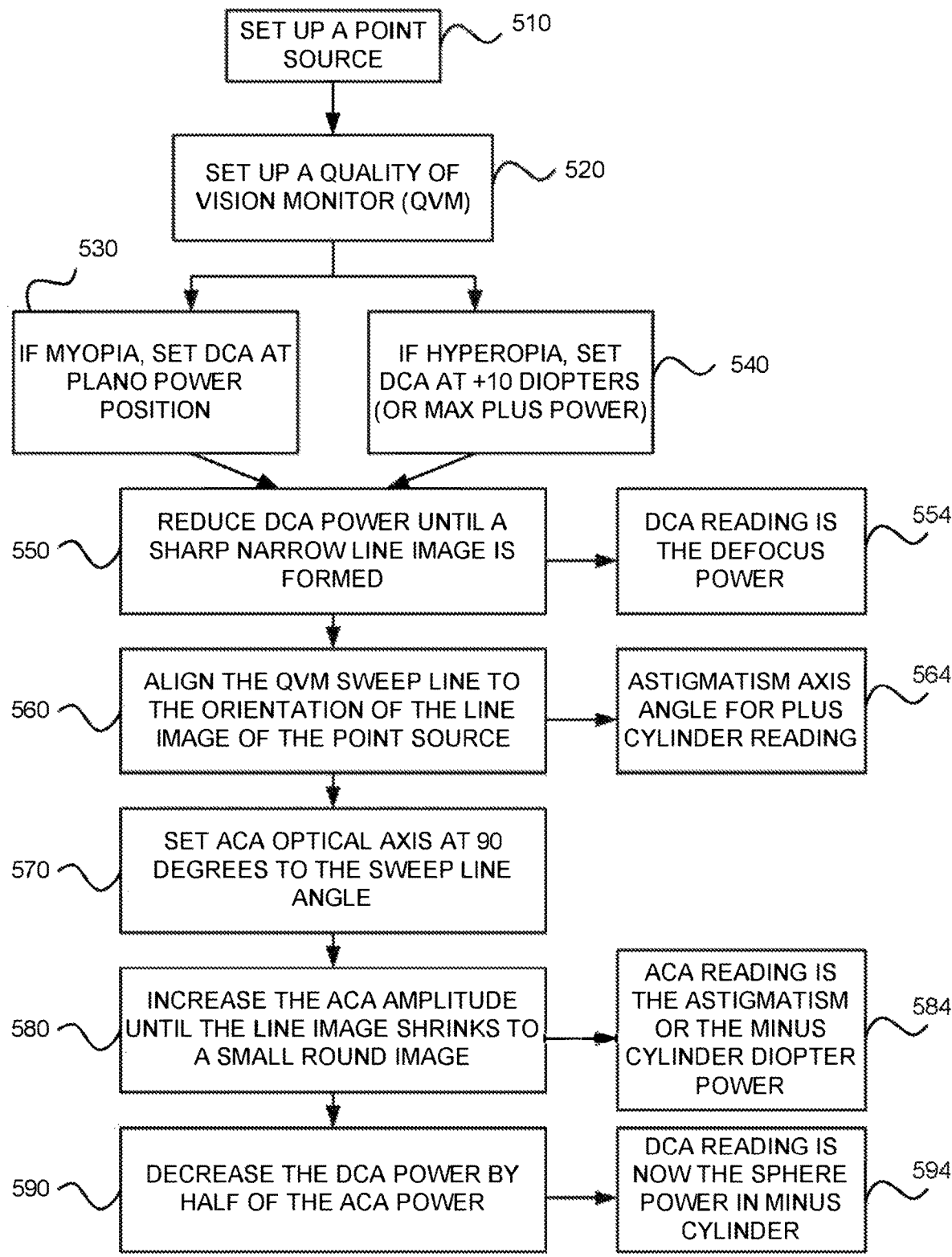
FIG. 3 is a flow chart illustrating a subjective refraction method in accordance with an embodiment.
Figure 4:
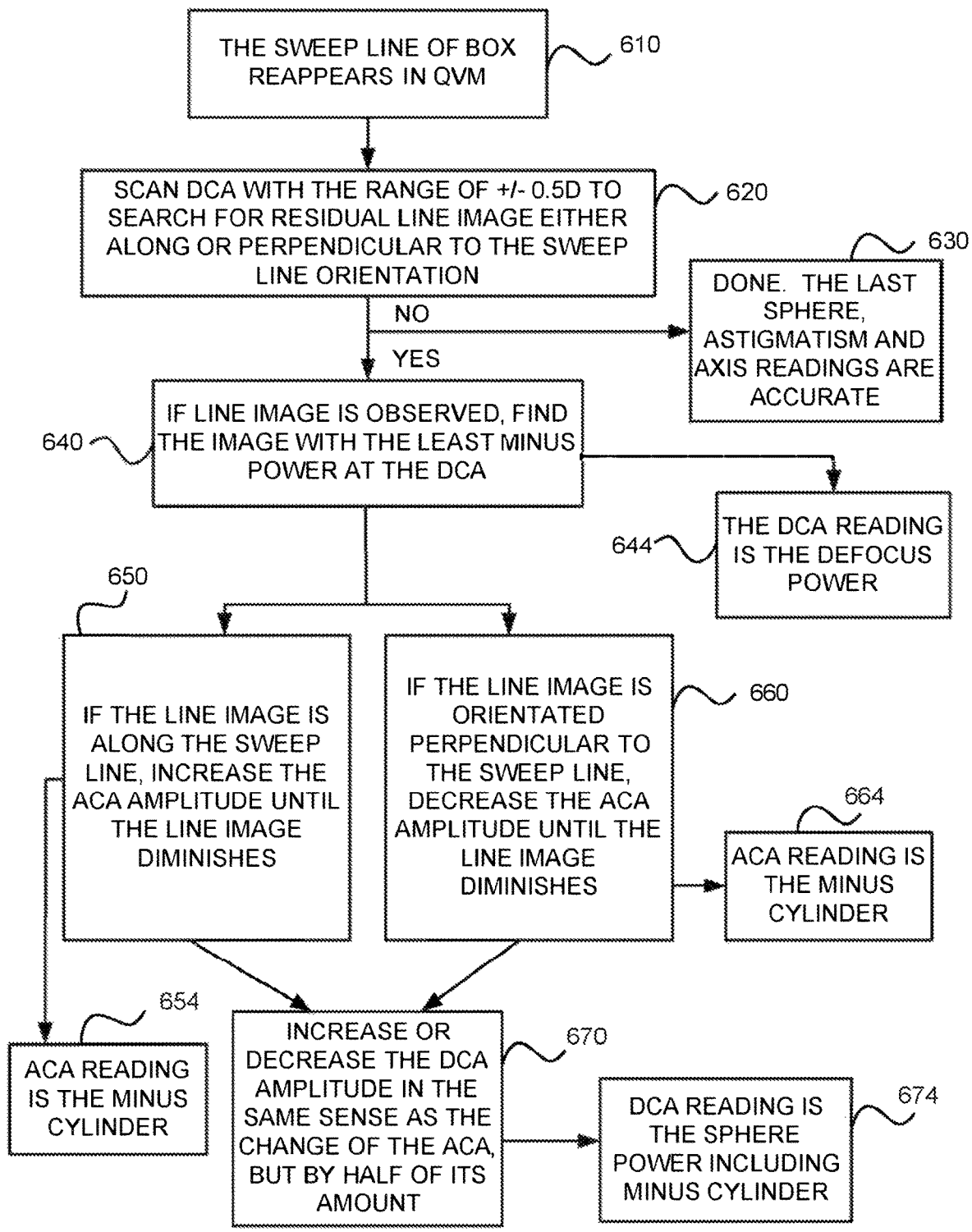
FIG. 4 is a flow chart illustrating a fine tuning of a subjective refraction method in accordance with an embodiment.
Figure 5:
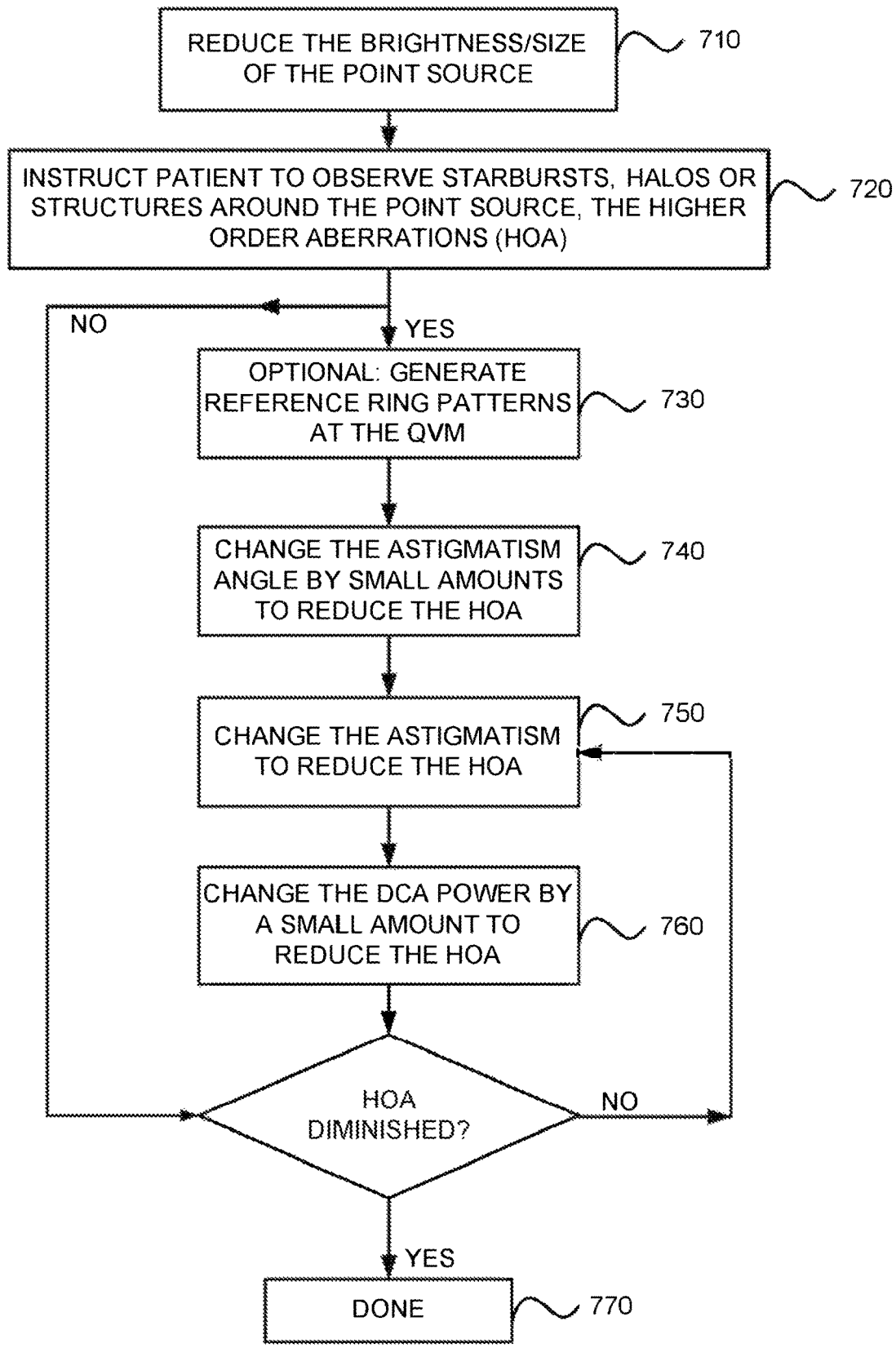
FIG. 5 is a flow chart illustrating correction of high order aberrations in accordance with an embodiment.

FIGS. 3-5 illustrate steps or operations or functions that may be performed in accordance with methods of preferred and alternative embodiments. FIG. 3 illustrates elements 510-594, FIG. 4 illustrates elements 610-674 and FIG. 5 illustrates elements 710-770. These may be performed in different orders and one or more may be skipped in alternative embodiments. These are also non-exhaustive examples, and additional steps, operations or functions may be added or replaced into the technique. Descriptions of these processes are provided in detail in the parent U.S. application Ser. No. 11/675,079, which is incorporated by reference.

Using Alternative Devices to Generate Adjustable Wavefront Profile

While devices and methods have been described in detail for performing subjective wavefront refraction using continuously adjustable wave plates of Zernike functions, the present invention is not limited to a particular type of continuously adjustable wave plates, such as the preferred embodiment that has been described above, namely, an adjustable assembly including two Zernike wave plates of identical, or approximately identical, first index, except that the second index is of opposite sign, Z(i,+/−j), where i and j are the first and the second indices respectively, of the Zernike function. In other embodiments, the continuously adjustable Zernike wavefront profile may be replaced by other wavefront profile generating devices and methods, such as a deformable mirror, a liquid crystal phase plate, or another suitable device that is capable of generating adjustable Zernike wave amplitude and angle. Alternative devices can be much more costly and complicated to operate for a clinical instrument.

The appropriate selected device is preferably placed at a conjugate plane of the patient's pupil or spectacle plane. In the case of using a liquid crystal wave plate, it is placed at the location of the previously described wave plate assembly. In one embodiment, during the refraction process for an optimal wavefront correction, again using the example above and assuming the ordered list is the optimal list, after the second order Zernike function wave plates have been optimized for the patient, the next Zernike function to be optimized is Coma. Again the patient is given two knobs for adjustment control, one to adjust the amplitude and one for the angle. The liquid crystal wave plate generates a Coma in accordance with the input from the control knobs, while the patient is looking at the target, which may be a nearly collimated light source, or other appropriate variation of the target.

So far this alternative process is substantially the same as described previously. Next, moving down the ordered Zernike list, the next step is to optimize the Trefoil. When a Trefoil wavefront profile is requested via signals generated from the patient's turning of knobs, the wavefront profile of the liquid crystal is to be changed to be the sum profile of the Coma amplitude and angle as arrived at from the last optimization for the Coma function. A computer or an appropriate microprocessor is to receive the input from the patient (the knobs in this case, but this is not a limiting factor), and computer routine will preferably perform the sum calculation of (1) the previously arrived at Coma wavefront (amplitude and angle) and (2) the requested Trefoil amplitude and angle. The resulting profile of the sum (Coma and Trefoil) is then sent to the liquid crystal wave plate controller, which generates electrical signals, each of which is to be directed to a specific location of the liquid crystal wave plate, and a two dimensional wavefront profile is then generated. When different signs are received from the knobs, a new Trefoil amplitude or angle is requested. This new Trefoil replaces the last Trefoil, and a new sum wavefront profile (old Coma and new Trefoil) is generated from the computer and is sent to the liquid crystal controller, and so forth, until optimal Trefoil is reached.

The process is then repeated for the next Zernike function down the ordered list. In this example, Z(4,+/−2), or the secondary astigmatism, is to be optimized for the same patient. When that is optimized, the next Zernike function in the ordered list is to be optimized, and so forth, until no improvement is perceived or perceivable by the patient and the optimization process is considered completed.

Alternative Method of Searching for Optimal End Point for Both Adjustable Wave Plates and Alternative Variable Wavefront Profile Generating Devices Such as Liquid Crystal Phase Plate or Deformable Mirrors In another embodiment, a quick and automated method is provided. Instead of providing the test subject with two knobs to control the angle and the amplitude independently, a computer program is used in this case to scan the angle of the wave plate continuously, at a given amplitude value of the Zernike wave plate. For example, an optimized trefoil is to be determined in a test. First, the amplitude of trefoil is set, e.g., at 0.2 microns, and the angle of the optic axis is scanned by the computer quickly. The test subject then presses an input device such as a mouse or a knob, or joystick, or executable display, or voice-activation, to indicate that he or she has seen an improvement point. Repeated scans may be used to check the reliability of the test subject's input for repeatability at or near the same angle or orientation of the wave plate. In one embodiment, if no appreciable improvement is indicated, or an improvement is indicated, the computer increases the amplitude and scans the angle as before. In this embodiment, the test is continued until the test subject presses a second input device indicating the target image quality has become worse rather than improved. Values of the amplitude and the angle at the best vision are noted, e.g., stored in a permanent or removable memory device or printed out on a report, display, or pdf.

Alternatively, if the test subject has confirmed the angle location accurately more than once, the angle orientation of the wave plate may be set at that orientation, and the computer then changes the amplitude, i.e. to increase, or decrease, again in a scanning fashion. The computer monitors the test subject's input to indicate image quality improvement or deterioration. This method substantially increases the test speed, and arrives at the end point of the sharpest image of the target more efficiently.

Figure 6:
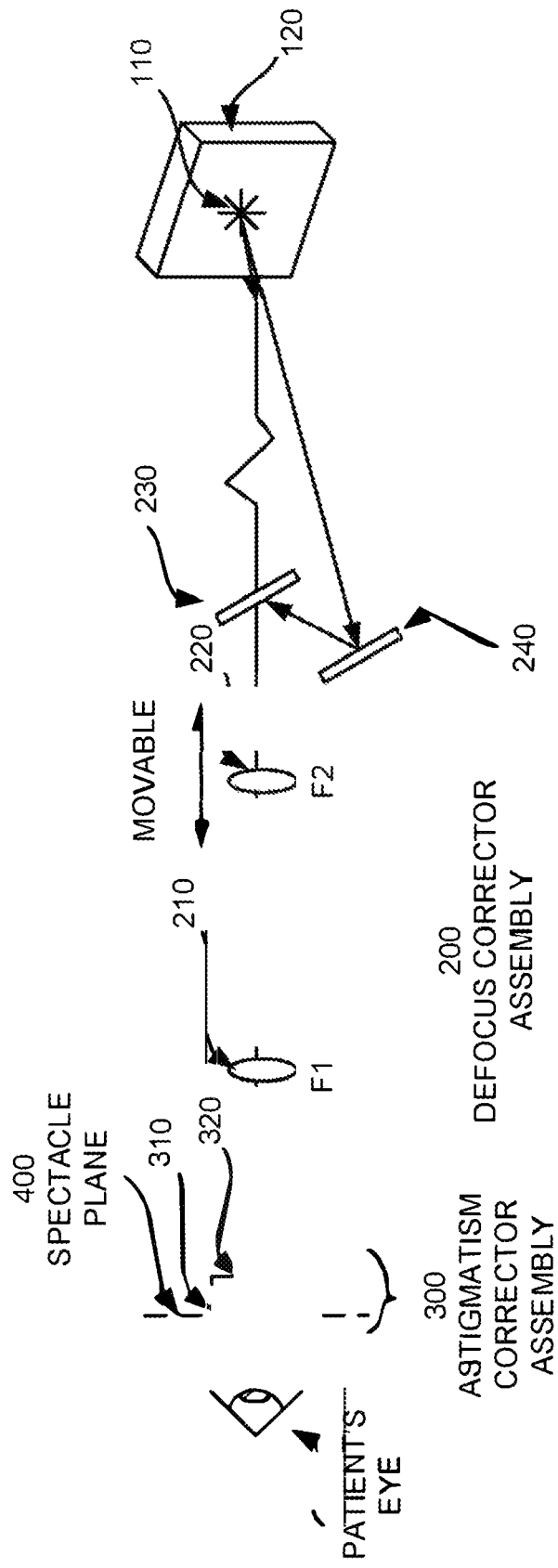
FIG. 6 illustrates a subjective refraction apparatus in accordance with another embodiment.

Referring now to FIG. 6, a deformable mirror 230 or curved reflecting optic 230 may be used, instead of a transmissive assembly such as a liquid crystal wave plate that was indicated as being located at plane 225 in FIG. 1. The wavefront is reflected from the mirror 230, rather than passing through a wave plate or an adjustable Zernike wave plate assembly located at plane 225 in FIG. 1. Reflective optics such as mirrors are to be added in the path of the line of sight of the patient to re-direct the traveling wave from the target to the patient. In FIG. 6, the front surface of a deformable mirror 230 is positioned at the conjugate focal plane of the patient's pupil, similar to the previously described technique. A difference is that a reflective surface of mirror 230 is nearly facing the lens f2, 220 of FIG. 6, or at least rays passing through lens f2 220 encounter reflective optic 230 along the optical path towards target 110. Mirror 230 is also tilted slightly to allow rays traveling along the light path to encounter a plane mirror 240 which is offset from the optical path between lens f2 220 and mirror 230. This offset prevents blocking by mirror 240 of the view between the lens f2 220 and the deformable mirror 230. The plane mirror 240 is also oriented along a path towards the target light source 110. A wavefront refraction technique uses a deformable mirror 230 that preferably serves a substantially same function as using a liquid crystal wave plate 225 (see FIG. 1), except electric signals are sent to actuators that deform the mirror surface to generate the requested shape to generate the optical path difference.

Electrical, Electronics Hardware and Computer Programs

Figure 9:
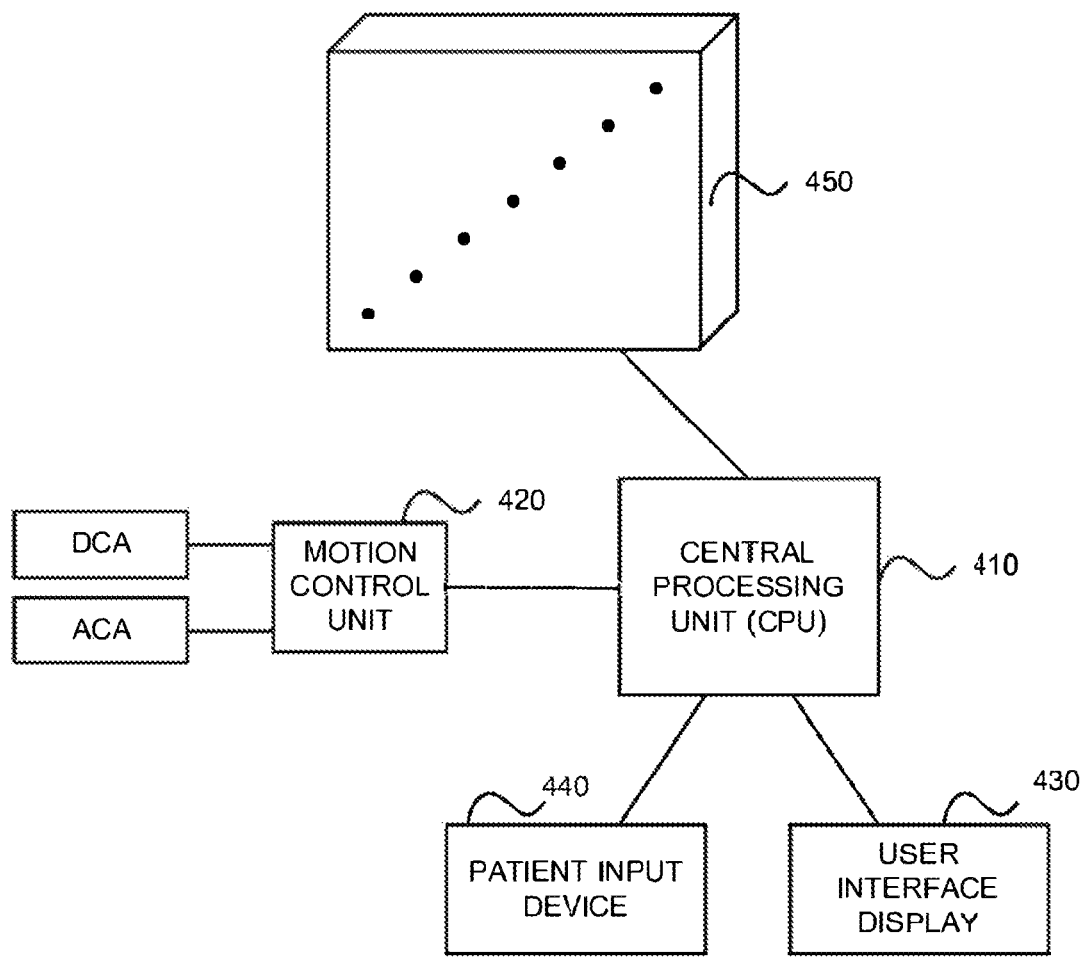
FIG. 9 illustrates a subjective refraction apparatus with electronic and/or software controls in accordance with an embodiment.

While the DCA and the ACA units can be adjusted manually, it is much more time efficient to have electrical and electronic hardware that connects a patient's input device such as push buttons and motors that move optical elements in the DCA and ACA, and/or use software to control the orientation of the sweep line or the generation of rings of various diameters at the QVM. These hardware and software components of an exemplary system are illustrated in FIG. 9. They preferably perform one or more of the following tasks.

A Motion Control Unit 420 may include a current amplifier and embedded electronics to direct the motion of the motors. It can drive the movement of one or more optical elements in the DCA, and/or ACA to change the defocus and/or astigmatism power and/or axis angle. It may also monitor the positional signal of the encoders at the DCA and/or ACA A User Interface Display 430 may include a display monitor, with or without touch screen capability. It displays the locations of the optical elements. The location information is to be obtained from an encoder attached to monitor the movement of lens 220, and likewise encoders for each of the rotary astigmatism plates at 310 and 320. It also displays a list of refraction procedure options such as optimizing defocus, astigmatism and/or locating the axis angle of the cylinder. It may also store and display an old prescription of a patient's eyeglasses or contact lenses, and/or those obtained with an autorefractor. By a touch of the screen or a clicking of a mouse, the DCA and/or ACA can be made to move to a pre-set prescription settings. These set locations may include a newly obtained, optimized prescription, an old eyeglasses prescription, or an autorefractor prescription. In this way, the patient can efficiently view and compare the quality of vision of two or more different prescriptions, thus advantageously adding another subjective or objective prescription component to the technique.

The Target 110, preferably a point source, can be generated on a computer monitor. The spot size, the display duration and its brightness may be controlled with computer software and/or a separate input device and/or monitor hardware control.

Items displayed at the QVM Monitor 450 may include multiple point sources, a line or multiple lines, multiple points on a line or on multiple lines. The displayed items may be programmed using software.

A Patient Input Device 440 can be joystick, a mouse, button, keyboard or keypad, voice-actuation, or a knob, or combinations thereof. The patient responds by clicking, pushing a button or turning a knob using hand or foot or other movement, or speaking a command such as start and/or stop, at the appropriate moment, to indicate the finding of a certain end-point, while the DCA and ACA positions are being scanned and while he/she is viewing the displayed items at the target 110, or other displayed items 122, 124, 126, 128 130 or combination thereof. A patient can also push a button, etc., to start to move an optic and stop pushing the button to stop movement of the object, thus affirmatively stopping movement of the optic by ceasing to move it.

A Central Processing Unit (CPU) 410 includes a computing processor. The unit stores motion control commands and other programmed subroutines to perform refraction procedures. It also presents graphics and items to be displayed at the target monitor 450. The CPU may perform any or all of the following tasks:

Collect and send data from and among a Patient Input Device, User Interface Display, QVM monitor, the Motion Control Unit, then to DCA and ACA units;

Convert location readings at the DCA and ACA to refractive powers in units of diopters. This can be accomplished with a software subroutine that has stored calibration information that relates position data to diopter powers;

Adjust the intensity of the point source by controlling the current to the light source or actuator that inserts and removes neutral density filters in and out of the beam path, while alternatively, if the point sources are from the QVM monitor, its intensity and size can be adjusted through programming.

Start and stop a sweeping motion of a sweep line using touch keys that electrically connect to the rotary drive mechanism of the sweep line. If the sweep line is generated on a QVM monitor, the sweep line or multiple point sources forming the line can be generated in a program.

Link to input/output ports, upload or download programs to an embedded processors;

Generate sweep line, parallel lines and/or rings or multiple points forming such patterns and at predetermined diameter or lengths at the QVM monitor;

Adjust the orientation of the sweep line, preferably in multiple speeds, e.g., a high speed mode and a high resolution, slow scan mode;

Set limits of travel range for the optics to avoid over-correction;

Automatically advance or decrease the DCA or ACA refractive power when such task is requested in a refraction procedure.

In FIG. 5, link and interaction among the various system components are indicated by connecting lines. That configuration is exemplary rather than limiting. For example, the Patient Input Device 440 may be linked to the Motion Control Unit 420, and the input signals from the patient can be routed through the Motion Control Unit 420 to the Central Processing Unit 410.

A Method of Wavefront Refraction Correcting Low Order Aberrations

A new refraction method is presented in the following. This method substantially differs from the current phoropter refraction method or autorefractor refraction. The method may utilize the structural components described above with reference to FIGS. 1(*a*)-1(*d*) and 9, or other suitable configurations.

First, a point source is set up to generate substantially plane wavefronts and is used as a viewing target, instead of a Snellen chart or a Landolt-C chart, or another eye chart.

At or near the spectacle plane 400 of a patient's eye, an Astigmatism Corrector Assembly (ACA) 300 is placed. Following after the astigmatism corrector, a Defocus Corrector Assembly 200 is preferably placed. Other optical arrangement may be understood by those skilled in the art to achieve the objectives illustrated at FIGS. 8A-8G, i.e., to adjust an image of a point light source from having spherical, astigmatic and/or higher order aberrations to substantially a sharp image of the point light source. A Quality of Vision Marker (QVM) may be generated, e.g., on a LCD monitor. The location, structure and function of these components have been described earlier.

An Automated Method of Finding an Optimized Corrective Lens Prescription

An automated refraction method is provided which has increased speed and user-friendliness of inventive device. The process aims to accomplish in stepwise manner reaching a number of end points leading to an optimized refraction correction within a predetermined accuracy level. The sphere, cylinder and axis values generated by the device and method may be used in a prescription for eyeglasses or other corrective lenses such as contact lenses or intraocular lenses. This subjective refraction correction may also be used to construct a corneal tissue ablation profile and to apply it in refractive laser surgery.

Figure 7:
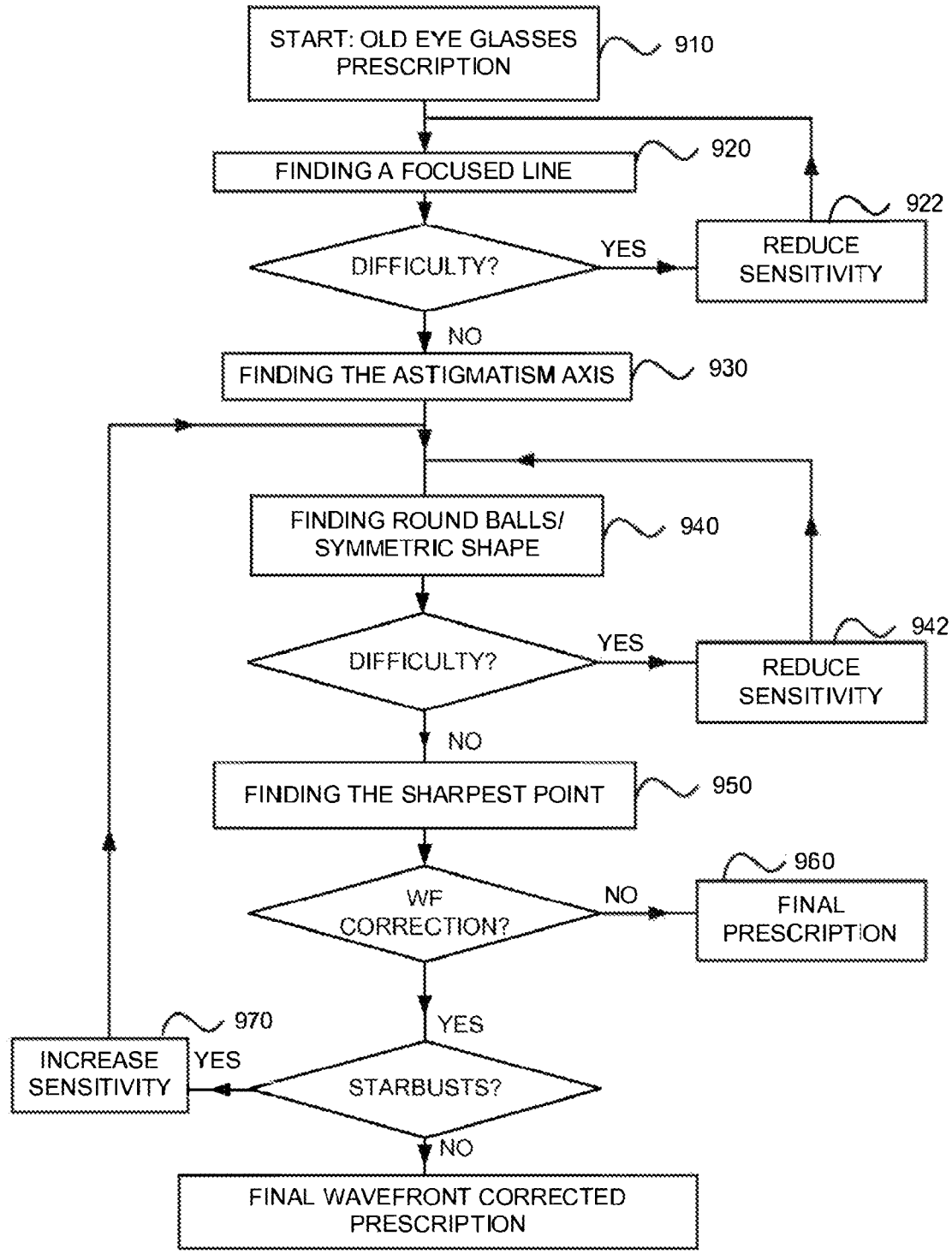
FIG. 7 is a flow chart illustrating a subjective refraction method in accordance with an embodiment.
Figure 8A:
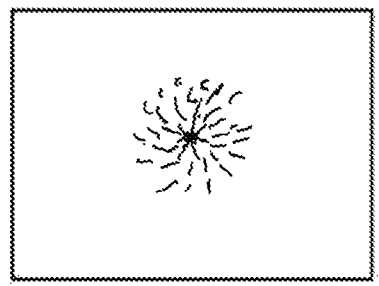
FIG. 8A illustrates an initially blurry image of the point light source in accordance with an embodiment.
Figure 8B:
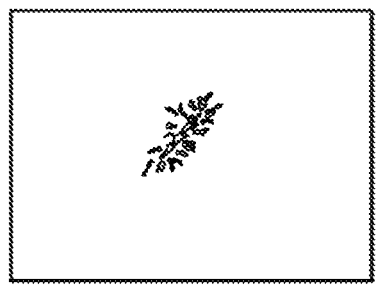
FIG. 8B illustrates the blurry image of FIG. 8A converging to a linear image.
Figure 8C:
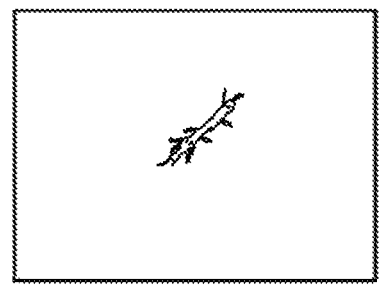
FIG. 8C illustrates a most substantially focused linear image indicated by a patient, still with spokes of light rays around it, in accordance with an embodiment.
Figure 8D:
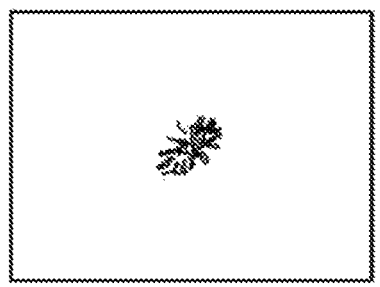
FIG. 8D illustrates the linear image of FIG. 8B being reduced in its long dimension and collapsing to form a round or oblong shape.
Figure 8E:
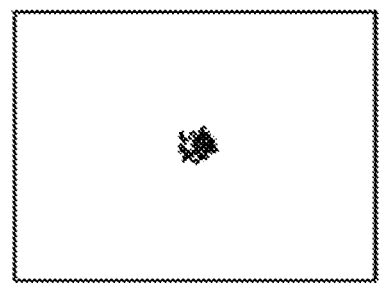
FIG. 8E illustrates an example of a most symmetric shape indicated by a patient in accordance with an embodiment.
Figure 8F:
FIG. 8F illustrates a focused point with starbursts as high order aberrations.
Figure 8G:
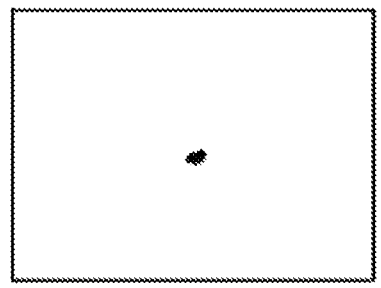
FIG. 8G illustrates the image of FIG. 8F corrected in accordance with an embodiment.

The automated refraction process includes finding specific end points. Some details have been provided above and thus are incorporated and not otherwise repeated here. Referring now to FIGS. 7 and 10:

Step 1: Finding a Focused Line, Box 920

Using old eyeglasses or autorefractor values, or an arbitrary or average location, e.g., a 20/20 location, as the starting point at Box 910, the Central Processing Unit (CPU) sets a start and end position for the DCA. For example, the old eyeglasses prescription may be −2.75 D, −1.50 D at 120 degrees; again a negative cylinder convention is used in the example. The CPU will first set the scan range to +/−1.50 D centering on −2.75 D, and the step size at 0.5 D. Therefore, the DCA will be set to scan from −1.25 D to −3.25 D in −0.5 D steps to increasingly minus diopter powers.

The CPU presents in the QVM monitor a point source for the patient to view, including a number of pixels, at maximum brightness intensity. The cluster of pixels preferably forms a round shape that appears as a point at a sufficiently far distance.

The patient is ready to start, e.g., with an input device in hand. The CPU commences the scan to bring the "point source" stepwise to a more sharply focused line to the patient. The patient pushes a button or a trigger at the Patient Input Device (PID), to indicate the best image of a focused line has been reached as shown in FIG. 10(*a*), 810. The length of the line depends on the extent of the astigmatism in that patient. The patient may indicate an optimal image in other ways such as by releasing a button or verbal signaling or signaling an exam coordinator who then pushes a button or otherwise.

Next, a nesting method is used to pin point the optimized value at the DCA. Based on this patient input, the CPU set the scan range to +/−0.75 D at the patient selected location at the DCA. For example, the patient picked −2.75 D. The new scan range is now −2.00 D to −3.50 D and the scan step size is reduced to −0.25 D. This time, the patient selected −3.0 D at the DCA. If a comparable refraction accuracy of a standard phoropter refraction procedure of 0.25 diopters is desired, one may stop here and record the sphere value for the patient. One may choose to continue to refine the accuracy to 0.125 D or even finer in a similar manner.

Each scan comprises of 7 presentation positions at the DCA. At one second per step of the presentation, the two scans will take about 15 seconds. One may skip the first scan of 0.5 D step if one is reasonably certain that the patient's refractive power has not changed beyond 0.75 D.

Step 2: Finding the Astigmatism Axis Angle, Box 930

Again, one may use the axis angle from the old eyeglasses, CPU present a series of dots or multiple point sources forming a line, similar to the line pattern shown in FIG. 1(c), except that the angle of rotation of the line relative to the center is set by the CPU to be at the old eyeglasses axis angle of 120 degrees. Now the patient sees a series of focused short lines, each centering at each of multiple points along a line pointing at 120 degrees. All angles are presented with the patient's perspective. The axis starts at the scientific minus x-axis. The doctor's perspective will convert that to positive x-axis.

Suppose that the actual cylinder axis of the patient is 135 degrees, not 120 degrees. Short focused lines at each of the dots will be pointing at 135 degrees, however, the center of the short lines are aligning along 120 degrees as shown in FIG. 10(b), 820. Patient is then instructed to rotate a knob in the PID to effect a rotation of the sweep line formed by a series of dots. When the direction of the line is aligned with the short line exhibited by the astigmatism of the patient's vision, the short lines overlap and form a "solid" line 830. Patient can easily fine tune the pointing direction by optimizing the "line" quality, with minimum or none of the short lines "sticking out" as shown in 830. Patient push a trigger to indicate the task done and the operator now marks the axis angle.

Figure 10A:
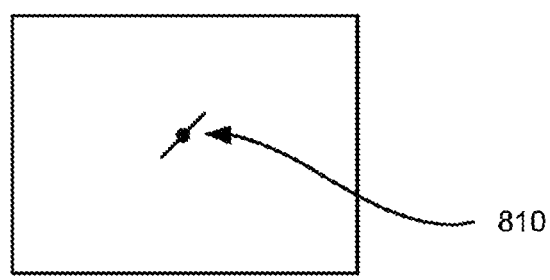
FIG. 10A illustrates a point with a small line through it representing a linear image appearing to a patient as adjusted from an initially blurry image of the point light source in accordance with an embodiment.
Figure 10B:
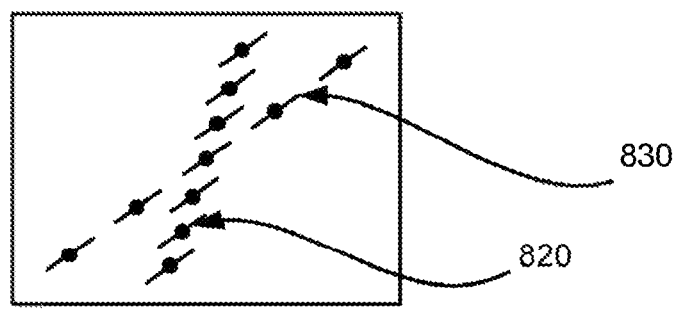
FIG. 10B illustrates a series of small line images arranged in a pair of crossed lines around an image of the point light source in accordance with an embodiment.

Note that the task of finding the angle of short line in FIG. 10(a) is made considerably easier by using a series of points and aligning them to the direction of the short line.

Moving the dotted line from 120 to 135 degrees by optimizing the quality of a line may take about 5 seconds.

Step 3: Finding Round Balls or Symmetric Shapes, Box 940

Figure 10C:
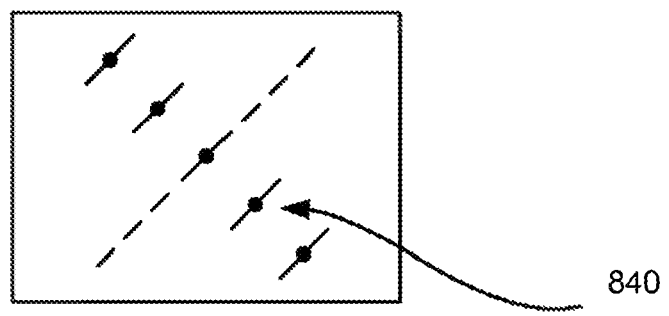
FIG. 10C illustrates a series of small line images arranged in a line and crossed with another line in accordance with an embodiment.
Figure 10D:
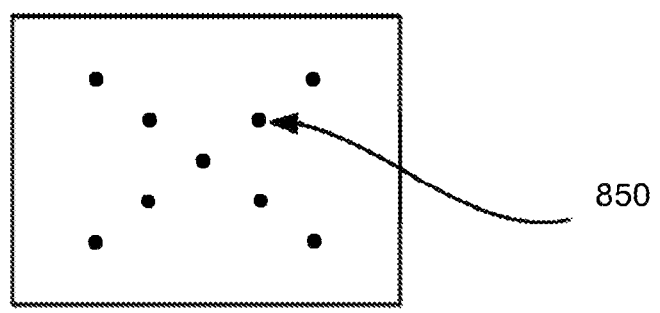
FIG. 10D illustrates two series of point images arranged in two crossed lines in accordance with an embodiment.
Figure 10E:
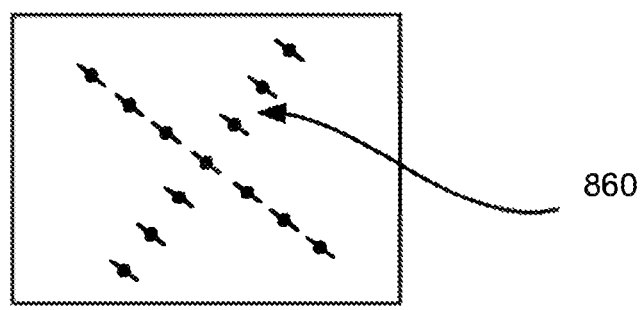
FIG. 10E illustrates a two series of short lines arranged in two crossed lines in accordance with an embodiment.

To neutralize the astigmatism errors, the patient is asked to turn the short lines into symmetrical or round light balls. CPU presents two cross lines of point or short line sources, as shown in FIG. 10(c). The two lines of points are pointing at 90 degrees cross, in one example, one line from the "Step 2" above, one line is pointing at 135 degrees (830) and one pointing at 45 degrees (840). At each point source, there is a short lines as in FIG. 10(a), 810, except now there are multiple points forming two cross lines, hence short lines arranged in a cross pattern.

The CPU uses the cylinder value of the old eyeglasses −1.50 D as a starting point, and set the scan range to +/−0.75 D in astigmatism diopter powers. In this example, it will cover from −0.75 D to −2.25 D in −0.25 D steps. The method is analogous to those in "Step 1" above. Patient will see a shortening of the focused lines initially, until it turns into round, symmetric balls. If too much astigmatism is applied, short lines will begin to develop in the 90 degrees direction to the original short lines, in the example, the 135 degrees short lines (840) turn into short lines pointing to 45 degrees in FIG. 10(e), 860. This can be used as an indication that ACA is providing too much astigmatism correction. At the optimal point of this step 3, the image as perceived by the patient, are round balls (850) along the two cross lines in FIG. 10(d). At this juncture, patient confirms that the task is done, and the operator marks the astigmatism power. For example, the best astigmatism value may be at −1.25 D.

The time to scan through the astigmatism is about 7 seconds. Therefore, the entire refraction process can be done in less than 60 seconds.

Step 4: Finding the Sharpest Point, Box 950

The CPU keeps the cross lines of round balls on the QVM monitor, or it may present just a single point as in FIG. 10(a) 810. The DCA is made to scan in −0.125 D steps from the final position from Step 1. The patient is expected to pick a DCA value when he or she sees the sharpest point when it is first formed. It should be at around half of the astigmatism value which is −0.625 D. To avoid over minus power, one may limit the maximum DCA move to no more than −0.5 D beyond the projected value of −3.625 D. One may pick the less minus position selected by the patient under repeated scanning at the DCA. For example the final sharpest DCA value may be at −3.75 D. Unless the patient wants to also correct the wavefront errors, the refraction procedure is completed and the optimized prescription for this patient is then Box 960 which may be −3.125 D sphere, −1.25 D cylinder at 135 degrees, in the example above.

Beneficial Applications

Once an optimized vision of a test subject has been arrived at, a wavefront correction for that person's eye is determined subjectively by the test subject. A correction wavefront profile may be used in a number of vision correction devices or surgery methods. When wavefront correction is used in eyeglasses, contact lenses, or intraocular lenses, the profile correction is typically incorporated by a construction of material thickness profile in such devices. When the wavefront refraction is used in surgical correction methods including PRK, LASIK, LASEK, and intra-corneal surgery, the wavefront correction is achieved by designing a tissue ablation profile either on the cornea or under the corneal flap, or inside the stroma via the use of a femtosecond laser as an example.

The present invention is not limited to the embodiments described above herein, which may be amended or modified without departing from the scope of the present invention as set forth in the appended claims, and structural and functional equivalents thereof: In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, the subject matter disclosed in all references cited above herein, in addition to the background and summary of the invention sections and including U.S. Pat. Nos. 5,984,916, 6,210,401, 6,325,792, 6,706,036, 6,761,454, 7,114,808, and 7,188,950, are hereby incorporated by reference into the detailed description of the preferred embodiments as disclosing alternative embodiments and components.

I claim:

1. A subjective refraction apparatus for generating a prescription for one or more corrective lenses of a patient, comprising:
  (a) a plane wave light source including substantially a point light source outside of a patient's eye as a viewing target;
  (b) at least one input device for the patient or for an examination administrator or both;

(c) an optical system disposed along an optical axis between the point light source and a patient's eye which initially forms a blurry image of the point light source at the patient's eye, (d) wherein the plane wave light source comprises a point source spaced apart from the patient a predetermined distance and having a predetermined diameter, or a substantially collimated light beam from a light source that simulates a point source of said predetermined diameter or less and spaced apart from the patient said predetermined distance, or both.

2. The subjective refraction apparatus claim 1, comprising a quality vision marker (QVM) comprising one or more display items including one or more lines, one or more circles, one or more points disposed along a pattern of one or more lines or circles, or combinations thereof.

3. The subjective refraction apparatus of claim 1, wherein the optical system comprises:

(i) a defocus corrector assembly (DCA) which causes a change of defocus power at the patient's eye; including a fixed lens and a lens that is movable along the optical axis using the at least one input device for adjusting defocus power, or a series of spherical lenses with incremental dioptric powers, or a combination thereof, until the patient indicates that the blurry image has become a relatively sharper linear image or a point image; and (ii) an astigmatism corrector assembly (ACA) which causes a change of astigmatism power or orientation of axis angle, or both, including a pair of astigmatism plates that are relatively adjustable or a series of cylindrical lenses, or a combination thereof, wherein the at least one input device is further for adjusting astigmatism power until the patient indicates that the linear image has become a substantially round or a point image.

4. The subjective refraction apparatus of claim 3, further comprising electrical or electronics hardware or computer programs, or combinations thereof, for performing individually or collectively one or more of the following tasks:

(i) driving movement of one or more optical elements in the DCA or ACA, or both, to change defocus or astigmatism power, or both;

(ii) displaying a location of an optical element;

(iii) converting a location or orientation reading, or both, to a refractive power in units of diopters;

(iv) collecting data relating to adjustments to the DCA and ACA;

(v) setting limits of movement range for the DCA or ACA or both to avoid over-correction;

(vi) automatically advancing DCA or ACA refractive power, or both, when such task is requested; or (vii) automatic aligning the ACA optical axis when such task is requested, or combinations thereof.

5. The subjective refraction apparatus of claim 1, further comprising a reference marker for providing a sweep line overlapping proximally with the light point source and having an orientation which is adjustable using the at least one input device until the patient indicates that the sweep line is aligned with the sharper linear image of the point source, thereby providing axis angle data of astigmatism errors of the patient's eye.

6. The subjective refraction apparatus of claim 5, wherein the marker further provides a display pattern including one or more points, rings or parallel lines or combinations thereof.

7. The subjective refraction apparatus of claim 1, wherein a laser source simulates a point source positioned two meters or farther away from the patient, and having a diameter of 2 mm or less.

8. The subjective refraction apparatus of claim 7, further comprising a lens which causes an image of the point source to appear to the patient to be two meters or farther away.

9. The subjective refraction apparatus of claim 1, wherein spectral contents of the light source comprise white light, substantially blue light, substantially yellow light, or substantially red light.

10. One or more spectacle, contact or intraocular lenses having a prescription generated by the subjective refraction apparatus of claim 1.

11. The subjective refraction apparatus of claim 1, comprising:

an optical adjustment interface for adjusting the optical system, wherein the optical adjustment interface is configured for adjusting the prescription for correcting higher order aberrations (HOA), including selecting a brightness of the point light source to avoid saturation or selecting the physical dimensions of the point light source, or both.

12. The subjective refraction apparatus of claim 1, wherein the optical adjustment interface is configured for searching until the patient indicates one or more end points including adjusting astigmatism correction amplitude to converge the blurry image in at least one dimension.

13. The subjective refraction apparatus of claim 12, wherein the optical adjustment interface is configured for adjusting defocus correction amplitude to reduce a long dimension of a substantially linear shape or to converge the substantially linear shape into a best possible symmetric shape, or to a focused point image, or combinations thereof.

14. The subjective refraction apparatus of claim 1, further comprising a reference marker for providing a sweep line overlapping proximally with the point light source and having an orientation which is adjustable using the at least one input device until the patient indicates that the sweep line is aligned with the sharper linear image of the point source, thereby providing axis angle data of astigmatism errors of the patient's eye.

15. The subjective refraction apparatus of claim 14, wherein the marker further provides a display pattern including one or more points, rings or parallel lines or combinations thereof.

16. The subjective refraction apparatus of claim 1, wherein a laser source simulates a point source positioned two meters or farther away from the patient, and having a diameter of 2 mm or less.

17. The subjective refraction apparatus of claim 16, further comprising a lens which causes an image of the point source to appear to the patient to be two meters or farther away.

18. The subjective refraction apparatus of claim 11, wherein spectral contents of the light source comprise white light, substantially blue light, substantially yellow light, or substantially red light.

19. The subjective refraction apparatus of claim 11, wherein the adjustable optical system comprises:

(i) a defocus corrector assembly (DCA) which causes a change of defocus power at the patient's eye, including a fixed lens and a lens that is movable along the optical axis using the at least one input device for adjusting defocus power, or a series of spherical lenses with incremental dioptric powers, or a combination thereof, until the patient indicates that the blurry image has become a relatively sharper linear image or a point image, or (ii) an astigmatism corrector assembly (ACA) which causes a change of astigmatism power or orientation of axis angle, or both, including a pair of astigmatism plates that are relatively adjustable or a series of cylindrical lenses, or a combination thereof, wherein the at least one input device is further for adjusting astigmatism power until the patient indicates that the linear image has become a substantially round or a point image; or (iii) combinations of (i) and (ii).

20. One or more spectacle, contact or intraocular lenses having a prescription generated by the subjective refraction apparatus of claim 11.

* * * * *